(12) United States Patent
Hacker et al.

(10) Patent No.: US 11,833,080 B2
(45) Date of Patent: Dec. 5, 2023

(54) PLANNING DEVICE AND METHOD FOR GENERATING CONTROL DATA FOR AN OPHTHALMOLOGICAL LASER THERAPY DEVICE FOR STRUCTURES BRIDGING THE CORNEA IN A PRESSURE-REDUCING MANNER

(71) Applicant: Carl Zeiss Meditec AG, Jena (DE)

(72) Inventors: Martin Hacker, Jena (DE); Mark Bischoff, Jena (DE); Christian Dietrich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 497 days.

(21) Appl. No.: 16/978,605

(22) PCT Filed: Mar. 5, 2019

(86) PCT No.: PCT/EP2019/055440
§ 371 (c)(1),
(2) Date: Sep. 4, 2020

(87) PCT Pub. No.: WO2019/170669
PCT Pub. Date: Sep. 12, 2019

(65) Prior Publication Data
US 2020/0405539 A1    Dec. 31, 2020

(30) Foreign Application Priority Data
Mar. 7, 2018   (DE) ...................... 10 2018 203 356.0

(51) Int. Cl.
*A61F 9/008*    (2006.01)
*A61F 9/007*    (2006.01)

(52) U.S. Cl.
CPC ...... *A61F 9/00802* (2013.01); *A61F 9/00781* (2013.01); *A61F 2009/00851* (2013.01);
(Continued)

(58) Field of Classification Search
CPC .. A61F 9/00781; A61F 9/008; A61F 9/00802; A61F 2009/00851;
(Continued)

(56) References Cited

U.S. PATENT DOCUMENTS

| | | |
|---|---|---|
| 3,788,327 A | 1/1974 | Donowitz |
| 5,807,302 A | 9/1998 | Wandel |

(Continued)

FOREIGN PATENT DOCUMENTS

| | | |
|---|---|---|
| DE | 11 2011 103 923 T5 | 8/2018 |
| DE | 10 2017 104 543 A1 | 9/2018 |

(Continued)

OTHER PUBLICATIONS

International Search Report and Written Opinion for PCT/EP2019/055440, dated Aug. 13, 2019, 20 pages.
(Continued)

*Primary Examiner* — Mallika D Fairchild
*Assistant Examiner* — Shreya Anjaria
(74) *Attorney, Agent, or Firm* — DeWitt LLP

(57) ABSTRACT

A planning device that generates control data for an ophthalmological laser therapy appliance with a laser device and a control unit, includes a first interface for supplying various data and a second interface for transferring the control data to the control unit of the ophthalmological laser therapy appliance, which is embodied to generate control data for a scanning pattern for the ophthalmological laser therapy appliance from the supplied data, by application of which scanning pattern a structure can be produced in the cornea, the limbus, and/or the sclera of a patient's eye. The planning device is embodied to generate from the supplied data, control data for the scanning pattern of this structure and/or a structure for receiving the shunt implant.

21 Claims, 9 Drawing Sheets

(52) U.S. Cl.
CPC ............... *A61F 2009/00865* (2013.01); *A61F 2009/00872* (2013.01); *A61F 2009/00882* (2013.01); *A61F 2009/00891* (2013.01)

(58) Field of Classification Search
CPC .. A61F 2009/00865; A61F 2009/00872; A61F 2009/00878; A61F 2009/00882; A61F 2009/00891
See application file for complete search history.

(56) References Cited

U.S. PATENT DOCUMENTS

| | | |
|---|---|---|
| 6,595,945 B2 | 7/2003 | Brown |
| 6,881,198 B2 | 4/2005 | Brown |
| 7,192,412 B1 | 3/2007 | Zhou et al. |
| 8,728,021 B2 | 5/2014 | Theodore Coroneo et al. |
| 2005/0043722 A1 | 2/2005 | Lin |
| 2007/0156079 A1 | 7/2007 | Brown |
| 2008/0277332 A1 | 11/2008 | Liu |
| 2009/0043242 A1* | 2/2009 | Bene ............... A61F 9/00781 606/108 |
| 2013/0103011 A1 | 4/2013 | Edward et al. |
| 2014/0236067 A1 | 8/2014 | Horvath et al. |

FOREIGN PATENT DOCUMENTS

| | | |
|---|---|---|
| WO | WO 2014/127242 A2 | 8/2014 |
| WO | WO 2015/136520 A1 | 9/2015 |
| WO | WO 2016/100500 A1 | 6/2016 |
| WO | WO-2016100500 A1 * | 6/2016 |
| WO | WO 2016/109639 A2 | 7/2016 |
| WO | WO 2016/149425 A1 | 9/2016 |
| WO | WO 2018/049246 A1 | 3/2018 |
| WO | WO-2018049246 A1 * | 3/2018 ............... A61F 9/00 |

OTHER PUBLICATIONS

English translation of ISR for PCT/EP2019/055440, dated Aug. 13, 2019, 3 pages.

German Search Report for 10 2018 203 356.0 dated Jun. 11, 2018, 10 pages.

English translation of IPRP for PCT International Application No. PCT/EP2019/055440, dated Aug. 13, 2019, 12 pages.

* cited by examiner

PLANNING DEVICE AND METHOD FOR GENERATING CONTROL DATA FOR AN OPHTHALMOLOGICAL LASER THERAPY DEVICE FOR STRUCTURES BRIDGING THE CORNEA IN A PRESSURE-REDUCING MANNER

RELATED APPLICATIONS

This application is a National Phase entry of PCT Application No. PCT/EP2019/055440 filed Mar. 5, 2019, which application claims the benefit of priority to DE Application No. 10 2018 203 356.0 filed, Mar. 7, 2018, the entire disclosures of which are incorporated herein by reference.

TECHNICAL FIELD

The present invention relates to a planning device for generating control data for an ophthalmological laser therapy appliance with a laser device for generating, focusing and scanning a pulsed laser beam in a tissue of a patient's eye for modifying, microstructuring or severing the tissue along the scanning pattern of the focus of the pulsed laser beam and a control unit for the control thereof by application of control data, the planning device comprising an interface for supplying various data and an interface for transferring the control data to the control unit of the ophthalmological laser therapy appliance, said planning device being embodied to generate control data for the scanning pattern from the supplied data, the scanning pattern rendering a structure in the tissue of patient's eye generable.

The present invention furthermore relates to a corresponding planning method for generating control data for an ophthalmological laser therapy appliance, in such a way that a corresponding structure can be generated with the aid of these control data, an ophthalmological laser therapy appliance, a shunt implant, a computer program product and a method for generating structure in the tissue of the patient's eye.

BACKGROUND

The use of implants, some of which have a filter membrane, for pressure-reducing bridging of the cornea for glaucoma treatment, implanted into the cornea, limbus or sclera in order to create a drainage path therein, is sufficiently well known. Documents U.S. Pat. No. 6,881,198 B2, WO 2016/149425 A1, US 2008/0277332 A1, US 2009/0043242 A1, U.S. Pat. No. 8,728,021 B2, U.S. Pat. No. 6,595,945 B2, U.S. Pat. No. 6,881,198B2, WO 2016/109639 A2, WO 2016/100500 A1, U.S. Pat. Nos. 5,807,302 and 3,788,327 are mentioned as representatives thereof.

All solutions that use this direct, potentially low resistance, and hence very advantageous drainage path are based on the manual introduction of the corneal implant for drainage purposes ("corneal shunt"). Such an implant, which is also referred to as a "shunt" (since it facilitates a drain or a short with fluid transfer) or, in a specific embodiment, as a "stent" (as it keeps a passage open), allows aqueous humor to drain from the anterior chamber of the patient's eye to the tear film on the front side of the cornea. This can bring about a significant reduction in the intraocular pressure (TOP). In order to be able to permanently effectively fulfill this purpose following the implantation, it is necessary that such a shunt implant is precisely positioned and well fixed.

It was found to be disadvantageous if the implant is perceived by the patient as a foreign body because this causes an irritation of the nerves in the cornea of the eye or of the eyelid. It is likewise disadvantageous if pathogens penetrate through the epithelium of the cornea between the implant and the surrounding tissue and may even reach into the anterior chamber in this way. This constitutes a significant safety problem when using corneal shunt implants.

It is furthermore advantageous for the implants to be designed such that the drainage path remains permanently functional, i.e., aqueous humor can flow from the anterior chamber through the channel in suitable amounts. Moreover, it is important that pathogens cannot penetrate through the drainage channel in the reverse direction. There are various solution approaches to this end. However, a frequent problem is that the function or safety of the implant can no longer be guaranteed after a certain amount of time. At this point, it has to be removed and replaced by a new implant. Where possible, such a replacement treatment uses the still existing incisions in the cornea, which were already produced for the previous implant. Alternatively, it is also possible to replace a part of the implant provided to this end.

An additional challenge in relation to shunt implants in the cornea is that the cornea typically only has a thickness of 500 μm. Consequently, a corresponding short and direct shunt implant only has a small contact area with the corneal tissue. Therefore, it is frequently not possible to keep these implants stable in their position. By contrast, the alternative use of holders or sutures requires significant outlay in the use thereof. This may also lead to restrictions in the functionality. In particular, these implants are no longer minimally invasive and often lead to eye irritations. Sometimes there are even restrictions in the field of vision.

In conclusion, the known shunt implants for the cornea for glaucoma treatment therefore have the following disadvantages:

- Non-secure hold of the shunt implant or large dimensions required for a secure hold.
- Complicated fixation of the implants, often by suturing, as a result of which these solutions cannot be considered to be minimally invasive.
- Great manual demands in the production of the preparatory incisions required for precise positioning in order to meet application criteria. Restrictions arise in shaping if mechanical tools are used, as do side effects due to the use of precisely these mechanical tools. These may lead to stress and the disruption in the tissue surroundings (cornea, lid). Therefore, disadvantages arise in the implementation of applicative targets such as tightness, position accuracy (in particular the axial position accuracy, i.e., depth positioning), stability and creation of the desired interactions between the surrounding tissue and the implant (e.g., the production of desired pretension).
- The drainage flow is not individually adaptable and can consequently not simply be adapted according to the course of the disease.

SUMMARY OF THE INVENTION

Example embodiments of the invention provide apparatuses and methods that avoid the aforementioned disadvantages of the prior art. In particular, a stable drainage is expected to be established directly through the cornea, the limbus, and/or the sclera, which drainage is safely and precisely positionable with, where possible, a further reduction in the dimensions thereof and, in particular, a reduction or avoidance of a foreign body sensation. Options allowing the drainage flow to be set or adapted on the basis of the course of the disease are advantageous.

It is known that a short pulse laser processing of the cornea can serve to introduce vision-improving implants into the cornea and position these accurately and in stable fashion there. An example of this is AcuFocus' KAMRA corneal inlay for improving near vision by way of a stop. However, no comparable solution is known for a shunt implant for a glaucoma treatment.

According to the invention, use is now made of an ophthalmological laser therapy appliance to enable a tissue of a patient's eye, in particular in the region of the cornea, the limbus, and/or the sclera, to bridge the cornea in pressure-reducing fashion. Specifically, this means the generation of a structure for pressure-reducing bridging of the cornea in the tissue of the patient's eye and/or a structure for receiving a shunt implant for pressure-reducing bridging of the cornea in the tissue of the patient's eye, in particular in a cornea, a limbus, and/or a sclera. Such an ophthalmological laser therapy appliance comprises a control unit for controlling the ophthalmological laser therapy appliance by application of control data and a laser device with a laser source for generating a pulsed laser beam, a focusing apparatus for focusing the pulsed laser beam on a focus, and a scanning apparatus for scanning the focus of the pulsed laser beam in the tissue of the patient's eye, in particular in the cornea, the limbus, and/or the sclera, for modifying, microstructuring or severing the tissue along a scanning pattern of focus spots of the focus of the pulsed laser beam in accordance with the control data. In one variant, a structure for pressure-reducing bridging of the cornea in the tissue of the patient's eye can be created by severing the tissue. However, in another variant, it is also possible, in principle, for the structure for pressure-reducing bridging of the cornea in the tissue of the patient's eye to be a pore zone, entirely without, or else possibly according to desire with, a modification of the tissue surrounding the pores (e.g., by changing cross-linking). A combination of both variants is also possible.

A structure for receiving a shunt implant is usually created by severing the tissue. However, incomplete severing of the tissue is also possible in exceptional cases, and so a last barrier remains, the latter being penetrated when the shunt implant is introduced.

A pulsed laser usable here can for example be a femtosecond laser or picosecond laser, the focused laser beam of which being able to separate the tissue of the patient's eye by photodisruption as a consequence of nonlinear absorption. In principle, for the purposes of structuring or at least partly modifying eye tissue, the use of a laser which generates laser radiation absorbed by the tissue in linear fashion (e.g., an excimer laser), generally for tissue processing by ablation, is also possible. However, it only offers limited possibilities as it must always work on the respective tissue surface. It is also advantageous if non-thermal laser processes are used for structure generation in order to reduce the stresses on the tissue of the patient's eye.

By contrast, scanning the focus of the pulsed laser beam in the interior of the tissue of a patient's eye, as may be performed, for example, using the focus of a femtosecond laser or a picosecond laser, also contains scanning on the surface of this tissue and therefore offers possibilities for generating the structure in a substantially more comfortable manner and in a manner adapted to the respective situation.

By way of example, femtosecond lasers usable to this end have a wavelength from the 750 nm to 1100 nm range. However, the use of femtosecond lasers at other wavelengths is also conceivable in principle. By way of example, a wavelength from the 375 nm to 550 nm range, or from the 250 nm to 367 nm range is also relatively easily realizable from a technical point of view, corresponding to doubling or tripling of the frequency of the femtosecond lasers that are currently preferred from a technical point of view. Femtosecond lasers from the 1020 nm to 1060 nm wavelength range have been established for many years for corneal applications and are used here in exemplary fashion.

The pulse duration of a femtosecond to picosecond laser usable here is for example selectable from a 50 fs to 5 ps pulse duration range. A pulse duration from a 100 fs to 1 ps range, in particular, is for example preferred, and a pulse duration from a 250 fs to 600 fs range is particularly preferred in another example embodiment.

The pulse energy of a femtosecond or picosecond laser usable here for example lies in a pulse energy range of 20 nJ-2 µJ. A pulse energy of approximately 130 nJ is particularly preferred according to another example embodiment.

The laser pulse repetition rate, i.e., the repetition rate of the laser pulses, is usually selected from a range from 10 kHz to 50 MHz; a laser pulse repetition range from a range of 200 kHz to 20 MHz for example.

The pulsed laser beam is focused in order to act at its focus, which is also referred to as a focus point. In reality, this focus point has a focus effective region, in which the tissue is altered by the interaction with the focused laser beam. However, since the pulsed laser does not emit continuously but transmits pulse-by-pulse and, during its operation, the laser beam is scanned through the tissue, this results in a scanning pattern of the pulsed laser beam with a multiplicity of so-called focus spots, with a focus spot characterizing the respective relative position of the focus point at the time of a laser pulse. Thus, a focus spot of the pulsed laser beam can be imagined to be a type of target point of a scanning pattern of the focus of the pulsed laser beam, to be guided through the tissue, for an individual pulse. Here, the scanning pattern, with its focus spots, maps the course of the focus scan of the pulsed laser beam in time and space.

Here, scanning the pulsed laser beam should be possible without restrictions in all three spatial directions x, y, z; i.e., the scanning apparatus should be designed accordingly to carry out both lateral scans in the x- and y-direction and z-scans along the optical axis of the pulsed laser beam.

The control data with which the control unit controls the ophthalmological laser therapy appliance comprise data in relation to the respective relative spatial position (x, y, z) and performance data (such as pulse energy, polarization, phase profile) of the laser as a function of time, and said control data consequently describe the scanning pattern.

The control unit, which generally uses the control data generated by a planning device, can access all controllable units of the ophthalmological laser therapy appliance in the process, in particular access the laser source, the focusing apparatus and the scanning apparatus. Here, it can have an integral or multi-part design and can communicate via wired or wireless communication paths with the controllable units of the ophthalmological laser therapy appliance and with the planning device—and optionally with further apparatuses of the ophthalmological laser therapy appliance and devices linked therewith.

A planning device for generating control data for the ophthalmological laser therapy appliance, the latter comprising a laser device with a laser source for generating a pulsed laser beam, a focusing apparatus for focusing the pulsed laser beam on a focus, and a scanning apparatus for scanning the focus of the pulsed laser beam in the tissue of a patient's eye, in particular in a cornea, a limbus, and/or a sclera, for modifying, microstructuring or severing the tissue along a scanning pattern of focus spots of the focus of the pulsed laser beam in accordance with the control data, and a control unit for controlling the ophthalmological laser therapy appliance by application of the control data, comprises an interface for supplying data and an interface for transferring the control data to a control unit of the ophthalmological laser therapy appliance. Here, it is embodied to generate from the supplied data control data for the scanning pattern of the focus in the tissue of the patient's eye, by application of which the ophthalmological laser therapy appliance is controllable.

According to the invention, the planning device now comprises an interface for supplying data of the characterization of the patient's eye, in particular of the cornea, limbus, and/or sclera of the patient's eye, and for supplying data of a model of a shunt implant for pressure-reducing bridging of the cornea and/or data of a structure, to be generated in the cornea, the limbus, and/or the sclera, for pressure-reducing bridging of the cornea.

In addition to the data of the characterization of the patient's eye mentioned here, it is however also possible to supply further characterization data, in particular of the structural type, for example characterization data of a measured shunt implant, or else specific targets of the surgeon which are relevant to the generation of the control data, for example the tissue regions that should be excluded, in surgeon or patient specific fashion, from processing with the pulsed laser beam.

A "shunt" is a drainage structure; consequently, a "shunt implant" is an implant facilitating drainage. In this case, this relates to a drainage of aqueous humor which, on account of illness, is not discharged naturally, i.e., not released into the bloodstream. If it is not possible to drain the aqueous humor, there is an increase in intraocular pressure which, in the long term, can damage the optic nerve and ultimately may lead to blindness (glaucoma).

Thus, a pathologically increased intraocular pressure is treated with the shunt implant and/or a structure for pressure-reducing bridging of the cornea, by virtue of ensuring that the excess aqueous humor in the interior of the eye is guided to the outside through the cornea, limbus, and/or sclera and consequently ensuring that the intraocular pressure can be balanced with the surroundings of the patient's eye to the intended extent.

"Pressure-reducing bridging of the cornea" or the "implant for pressure-reducing bridging of the cornea" includes the option of bridging via the limbus, i.e., the edge region between cornea and sclera, and/or via the sclera: So as not to disturb vision, the pressure-reducing bridging of the cornea should not be implemented in the inner region of the cornea in any case; rather, this should be implemented in an outer region of the cornea, or else in the limbus and/or sclera. The object of pressure-reducing bridging of the cornea is achieved if a solution is created, by application of which it is possible to compensate a pathological increase in the intraocular pressure by an accumulation of aqueous humor that cannot be drained naturally.

In one variant, the data of a model of a shunt implant can be selected and called from a multiplicity of models of shunt implants in a database or so-called "lookup table" (LUT). Here, they may also already contain possible structures realizable in the tissue of a patient's eye—fitting to the respective shunt implant model. The same applies, in addition to or in place of a shunt implant, to the realizable structures in the corneal tissue, limbic tissue, and/or scleral tissue for pressure-reducing bridging of the cornea: Here, standard variants can be called from a database and are then adapted to the individual conditions in the patient's eye to be treated.

However, in another variant, the data of the model of a shunt implant for pressure-reducing bridging of the cornea can likewise be ascertained specifically for the individual case by way of various measurements and can be transmitted to the planning device. Thus, the required data of the model of a shunt implant can be supplied with the specific patient data or as process planning data that still is not patient-specific.

In a further—very rudimentary—variant, the data of the model of the shunt implant can be entered by way of an input mask.

Furthermore, according to the invention, the planning device is embodied to generate control data for the scanning pattern of the focus of the pulsed laser beam in the tissue of the patient's eye, in particular in the cornea, the limbus, and/or the sclera, from the supplied data—i.e., the data of the characterization and the data of the model of a shunt implant for pressure-reducing bridging of the cornea and/or the data of a structure, to be generated in the cornea, the limbus, and/or the sclera, for pressure-reducing bridging of the cornea. These control data render the ophthalmological laser therapy appliance controllable in such a way that the structure for pressure-reducing bridging of the cornea can be generated in the tissue of the patient's eye and/or the structure for receiving the shunt implant for the pressure-reducing bridging of the cornea can be generated.

Thus, according to the invention, a pressure in the interior of the eye chamber is reduced by application of a structure—with or without a shunt implant being received—generated by the ophthalmological laser therapy appliance.

If a structure for receiving a shunt implant is generated, this is for example implemented with an accurate fit: Since the model of the shunt implant is used to generate the control data for the scanning pattern of the focus of the pulsed laser beam, the structure for receiving the shunt implant can be produced therefrom with a very accurate fit, representing a decisive advantage over the method according to the prior art: The structure for receiving the shunt implant can therefore be kept as small as possible and can be designed in terms of its shape in such a way that it can be precisely positioned and oriented. Additionally, this can ensure that during use—i.e., following the insertion of the shunt implant in the cornea, the limbus, and/or the sclera—the structure for receiving the shunt implant has no openings next to the shunt implant in the cornea, the limbus, and/or the sclera. This reduces the risk of infection and further accelerates wound healing. The entire process of generating the structure for receiving the shunt implant and introducing the shunt implant is thus simplified since the structure for receiving the shunt implant and the shunt implant are then designed to fit to one another.

Here, a "tight fit" generation of a structure for receiving the shunt implant need not reproduce the data of the model of the shunt implant true to scale. Rather, the targeted control of a difference in scale, between the structure to be generated in the tissue and the shunt implant to be inserted, by way of correspondingly generated control data for the ophthalmological laser therapy appliance can be used to define a sealing pressure (pretension) of the tissue surroundings in relation to the shunt implant, which sealing pressure arises following the implantation of the shunt implant.

In conclusion, it is therefore proposed to use an ophthalmological laser therapy appliance to establish tissue modifications, microstructures, and/or perforations or incisions (the terms "incision" and "perforation" are used synonymously below) in the cornea, the limbus, and/or the sclera and hence establish a connection between the tear film and the anterior chamber of the eye, which allows drainage of aqueous humor.

The technique of laser processing, in particular using a laser therapy appliance as described herein, allows planar, flat or curved incisions or tissue changes to be performed very exactly and within the meaning of microstructuring. That is to say, the positioning of incisions and the relative position with respect to one another can be implemented on the scale of individual cell layers and consequently with an accuracy down to a few micrometers.

Furthermore, the processing of the tissue of the patient's eye, in particular of the cornea, the limbus, and/or the sclera, can be implemented with flexible and spatially precise shaping such that the insertion of a correspondingly complementarily formed microimplant is implemented with a very high positioning accuracy (10 μm) and with the desired orientation in the tissue of the patient's eye. What this processing approach can achieve is that an optimal three-dimensional structure is generated in the tissue of the patient's eye, in particular in the cornea, limbus, and/or sclera, for receiving the shunt implant—as it were as a "frame" for a microshunt which is inserted into this structure and then remains inserted there with a tight fit and in stable fashion. Tissue separated from the surroundings by incisions can also be taken for the purposes of producing this three-dimensional "frame".

Not least, this processing approach allows the generation of a defined reservoir for receiving aqueous humor, said reservoir serving as an element in the drainage chain, and thus implements a treatment of dry eyes or an intraocular pressure reduction.

The incisions for generating the structures are performable quickly, precisely and in automated fashion by application of the pulsed laser beam in order to create a desired perforation for draining aqueous humor via the cornea and/or in order to reliably and stably position a minimally invasive shunt implant, in particular a very small such implant, in the cornea. Typically, these can be generated in a laser time of less than 100 s and can comprise structure dimensions of less than 1 mm$^3$, for example less than 0.25 mm$^3$.

The planning device according to the invention is for example embodied in such a way that the scanning pattern describes at least one incision surface, which is filled by focus spots of the focus of the pulsed laser beam, which moves along the scanning pattern, in such a way that there is complete or incomplete separation of the tissue at this incision surface, and/or the scanning pattern describes at least one tissue region that has been microstructured or altered in its properties by the pulsed laser beam, said tissue region being filled by focus spots of the focus of the pulsed laser beam, which moves along the scanning pattern, in such a way that the tissue of this tissue region is modified in a focus effective region around the focus spot of the pulsed laser.

An incision surface determined by the scanning pattern can be curved multiple times in space and can be curved in different directions. The incision surface can be an open incision surface or else closed on itself, such as a lateral surface of a channel through the cornea, for example.

A complete separation of the tissue in the corresponding incision surfaces is implemented if the focus effective regions of the focus spots of the pulsed laser beam are overlaid in such a way that no tissue bridges or, at best, only a few tissue bridges that are separable, easily and without perceivable resistance, using surgical tools or using the shunt itself remain between the focus spots.

A microstructured tissue region is a three-dimensional structure in which the tissue is modified, but not separated, by the action of the pulsed laser beam. Usually, a local plasma arises, for example as a result of photodisruption, with the gas bubbles arising in the process slowly escaping from the tissue. The tissue is also modified in the edge regions of the focus effective region. This changes the permeability of the corresponding microstructured tissue region in relation to the untreated tissue. In order now to generate a microstructured tissue region, it is possible in each case to place a group of a plurality of focus spots tightly together in this tissue region and separate these from a further group of focus spots placed tightly together in this tissue region such that a true microstructure arises. Or else, the focus spots are separated so far apart from one another in the tissue region to be modified that no incision effect or tissue separation effect arises but that the tissue region is altered in terms of its properties, such as, e.g., the permeability of the aqueous humor through a corresponding tissue region in the cornea.

Here, following the irradiation by the pulsed laser radiation, the incision surface or the microstructured tissue region can have a different perforation in different regions of the incision surface and/or of the microstructured tissue region.

The intervention and hence also the planned structures are therefore distinguished in one configuration by virtue of there being a combination of a minimally invasive shunt implant and a three-dimensional microstructured cornea perforation such that the shunt implant functionally engages only in portions of the drainage system, e.g., in order to exert filtering effects, ensure the pressure drop or suppress the ingress of germs into the anterior chamber.

Furthermore, it is advantageous, for example, if the planning device is configured to generate control data in order to embody the structure for receiving the shunt implant for pressure-reducing bridging of the cornea in such a way that the shunt implant is receivable in such a way that a subsequent change in the position thereof in the cornea, the limbus, and/or the sclera is prevented, in particular in such a way that back-sliding following the reception thereof is prevented.

Particular positioning reliability is achieved, in one configuration of the planning device according to the invention, if the control data are generated in such a way that the structure for receiving the shunt implant for pressure-reducing bridging of the cornea is embodied as a "negative" of the shunt implant. In this respect, reference is made, in particular, to the above-described tight fit but lack of dimensional accuracy: Here, the structure for receiving the shunt implant can be generated with a targeted dimensional difference, i.e., slightly smaller than corresponding to the dimensional data of the model of the shunt implant, as a correspondingly reduced-size "negative" so that, following the implantation of the shunt implant into the elastic eye tissue, there is a sealing pressure, i.e., a pretension of the tissue surroundings in relation to the shunt implant.

This facilitates an insertion with a very accurate fit and creates a good and secure hold of the shunt implant in the structure.

Particular interest is directed to a configuration of the planning device in which the control data are generated such that the structure for receiving the shunt implant for pressure-reducing bridging of the cornea is embodied as a bridge-like structure in the cornea, the limbus, and/or the sclera, in which the shunt implant can for example be received completely, i.e., without a protrusion, in a specific configuration as an implant bridge structure.

This means that control data for a complex structure for receiving the shunt implant for pressure-reducing bridging of the cornea, which has a bridge structure or else multiple bridge structure, and, in one variant, also for a structure for pressure-reducing bridging of the cornea in the tissue of the patient's eye, which assists the function of the shunt implant, are generated in the planning device from the supplied data in order to ensure stable and function-maintaining positioning in the cornea for an implant with a plurality of drainage channels, which are connected via bridges.

The corresponding structures—of any type—in the tissue of the patient's eye are for example situated in the cornea in this case, albeit outside of the optical zone of the cornea, near the limbus or in the limbic region. Optionally, these may also reach into the sclera or else be laid there in order to avoid negative effects on the vision, it should however be noted that a corresponding laser treatment in the edge regions of the cornea is the most reliable and precise process for generating such structures for pressure-reducing bridging of the cornea and/or for receiving a shunt implant on account of the technical possibilities of current ophthalmological laser therapy appliances. Depending on the goal of the therapy, a plurality of such structures can be laid at a plurality of points in the tissue in the patient's eye—i.e., the planning device can be embodied to generate the control data for a plurality of such structures. Incidentally, the treatment at different points of the cornea, the limbus, and/or the sclera can also be repeated at intervals in order to set parameters such as the flow rate (of the aqueous humor) and/or adapt these in accordance with the course of the disease.

In one configuration of the planning device, the latter is furthermore embodied to generate, for a subsequent step, further control data for driving the laser device to scan the focus of the pulsed laser beam in (or else on) a shunt implant for pressure-reducing bridging of the cornea, received in the patient's eye, for the purposes of modifying the shunt implant along a scanning pattern of focus spots of the focus of the pulsed laser beam in accordance with the control data.

According to an example embodiment, a planning device configured to generate the further control data for the subsequent step in such a way that protrusions of the shunt implant received in the tissue of the patient's eye are removed and/or the shunt implant is smoothed is particularly advantageous.

Thus, in this configuration, the shunt implant is likewise processable by application of the laser device following the insertion of said shunt implant into the cornea, the limbus, and/or the sclera of the patient's eye, for the purposes of which the planning device likewise creates appropriate control data. As a result, components on the installed shunt implant can be processed, for example in order to ablate protrusions and thus, for example, avoid potential causes for an irritation of the eyes. This can also achieve corneal smoothing, reducing an irritation of the lid.

It is moreover very important that, by application of laser processing by the laser device of the ophthalmological laser therapy appliance, there is the option of processing, in microscopic dimensions, the once structured tissue of the patient's eye or the shunt implant in such a way that these being overgrown by the constantly growing epithelial cell layers is prevented. The adaptation can also be implemented individually for the patient by way of the available precision of the proposed laser processing. It allows temporal and repeated adaptation of the shunt implant and/or of the structure for pressure-reducing bridging of the cornea in the tissue of the patient's eye on the basis of the course of the disease or the patient's development. By way of example, the flow rate through the shunt implant can be adapted by laser processing.

In another configuration of the planning device, provision is made for the structure for pressure-reducing bridging of the cornea to have a drainage structure, which is stabilized by way of light-induced cross-linking. Thus, a process of light-induced cross-linking is also included when generating the control data for the ophthalmological laser therapy appliance.

In particular, this is an option if, for the purposes of guaranteeing a stable drainage of the aqueous humor, a stable drainage structure should be established over a relatively long period of time, i.e., for example, a period of time of more than one year, even without a shunt implant, i.e., only with a structure, generated in the tissue of the patient's eye, for pressure-reducing bridging of the cornea. In particular, there can be an individual adaptation to the patient or to the clinical picture by way of appropriate light-induced cross-linking. Here, the processing—as a rule, in the region of the stroma of the cornea—is carried out in such a way that an ingress of bacteria or germs is prevented; this is facilitated, in particular, by way of three-dimensional microstructuring using the laser device of the ophthalmological laser therapy appliance.

Chemical cross-linking of the processed tissue structures by irradiation, for example by adding riboflavin, can also be used to reduce undesirable scarring or wound healing reactions.

In a further configuration, the planning device according to the invention is configured to moreover define at least one access incision from the supplied data, said access incision reaching from the surface of the cornea, the limbus, and/or the sclera to the structure for pressure-reducing bridging of the cornea and/or to the structure for receiving the shunt implant for pressure-reducing bridging of the cornea, and generate additional control data for driving the laser device for this access incision, by application of which the ophthalmological laser therapy appliance is controllable in such a way that this access incision can be generated in the cornea, the limbus, and/or the sclera of the patient's eye.

Thus, in addition to the generation of the structure for pressure-reducing bridging of the cornea and, in particular, for receiving a shunt implant for pressure-reducing bridging of the cornea, further processing or fixation incisions are introduced very precisely into the cornea, the limbus, and/or the sclera, said incisions allowing the shunt implant to be locked into the cornea, the limbus, and/or the sclera using appropriate fixation elements. To this end, the shunt implants may be multi-part and have reversible connection or fixation elements and mechanisms which facilitate the exchange of individual elements. The further processing or fixation incisions are generated earlier than, later than or simultaneously with the actual structure.

In one embodiment of the planning device, the structure for pressure-reducing bridging of the cornea has a cavity and the planning device generates control data for the scanning pattern in such a way that these render a tissue volume in the cornea, the limbus, and/or the sclera separable, said tissue volume for example subsequently being removable through the opening of an access incision.

It is also possible for a reservoir for receiving liquid (aqueous humor) to be defined when generating a structure for pressure-reducing bridging of the cornea and/or a structure for receiving a shunt implant for pressure-reducing bridging of the cornea, said reservoir serving as an element in the drainage chain, and for additional control data to be generated for said reservoir within the scope of generating the control data for the structure for pressure-reducing bridging of the cornea, said additional control data allowing this reservoir to subsequently be realized by the laser device of the ophthalmological laser therapy appliance. Removability of the separated tissue volume is necessary for generating a cavity in the tissue of the patient's eye.

The structures to be generated for pressure-reducing bridging of the cornea and/or for receiving the shunt implant and/or the access incision can be positioned on the basis of a registration image of a patient's eye or on the basis of a section thereof. The shunt implant can also be modified with the aid of a registration image of the patient's eye.

A planning device with an interface, to which a measuring device is connected is advantageous, according to an example embodiment, said measuring device producing the data of the characterization of the patient's eye from a measurement of the patient's eye and supplying said data of the characterization to the planning device, wherein the measuring device for example comprises one or more of the following apparatuses: autorefractor, refractometer, keratometer, aberrometer, wavefront measuring device, optical coherence tomography (OCT) scanner, Scheimpflug camera, ultrasound imaging system, microscope.

Depending on the ophthalmological laser therapy appliance and measuring device, an active correction of the control data by the planning device is also possible if the measuring device and laser device represent a functional unit in the ophthalmological laser therapy appliance and both are able to access the patient's eye, either simultaneously or successively after short intervals, provided the planning device is connected by way of appropriate active communication paths via the interfaces to the laser device and, in particular, to the control unit of the laser device and to the measuring device.

Such communication paths can be wireless or wired data links. If an active control and correction during the laser therapy step is excluded, it is also possible to transfer the control data from the measuring device to the planning device and/or from the planning device to the laser device by application of a data medium.

In particular, the planning device can comprise a display device for visual representation of the control data and an input device for subsequent alterations of the control data.

In a further example configuration of the planning device, the latter is embodied within the scope of generating the control data to take account of a deformation of the cornea, of the limbus, and/or of the sclera of the patient's eye during laser therapy by way of an apparatus for immobilizing the patient's eye, in particular a deformation of the cornea, the limbus, and/or the sclera as a result of affixing the patient's eye to the ophthalmological laser therapy appliance by application of a patient interface, optionally a contact glass or a liquid patient interface, such that the structure for pressure-reducing bridging of the cornea and/or the structure for receiving the shunt implant for pressure-reducing bridging of the cornea is present in the non-deformed cornea, limbus, and/or sclera.

An ophthalmological laser therapy appliance for treatment of a tissue of a patient's eye for pressure-reducing bridging of the cornea comprises a laser device with a laser source for generating a pulsed laser beam, a focusing apparatus for focusing the pulsed laser beam on a focus, and a scanning apparatus for scanning the focus of the pulsed laser beam, for example in all three spatial directions x, y, and z, in a tissue of a patient's eye, in particular in a cornea, a limbus, and/or a sclera, for modifying, microstructuring or severing the tissue along a scanning pattern of focus spots of the focus of the pulsed laser beam, which is determined by control data, and a control unit for controlling the ophthalmological laser therapy appliance by application of the control data.

Possible configurations of the laser device have already been described above; the control unit, too, was already characterized in more detail above in terms of possible configurations and interactions.

In the simplest case, a focusing lens serves as a focusing device; however, as a rule, the focusing device is configured as a lens system with stationary and/or movable lenses.

A scanning apparatus employable here can have very different configurations: In a very simple configuration, the scanning apparatus contains a lateral scanner, for example a combined xy-scanner or an x-scanner and y-scanner, which can operate independently of one another, or an R-scanner, which is rotatable about an axis extending parallel to the optical axis, and a z-scanner for shifting the focus of the pulsed laser beam along the z-direction (i.e., along the vertical), which extends parallel to the optical axis. More complex configurations of the scanning apparatus can each have a fast and a slow scanner for each spatial direction x, y, z. The arrangement of these scanners with respect to one another can vary and plays no essential role in the invention. Scanning "in a tissue" also comprises scanning directly on the surface of the tissue.

According to the invention, the ophthalmological laser therapy appliance moreover comprises an above-described planning device for generating the control data.

As already described above, femtosecond or picosecond lasers are for example used in such a laser therapy appliance in order to separate, modify or microstructure a tissue of a patient's eye by application of photodisruption processes. However, use can also be made of a pulsed laser beam for the ablation or coagulation processes.

The lateral incision accuracy is approximately 3 μm; as a rule, the positioning accuracy of individual incisions within a structure relative to one another is better than 20 μm, in another example embodiment better than 5 micrometers.

An example configuration of the ophthalmological laser therapy appliance moreover comprises a measuring device for generating data of the characterization of the patient's eye, in particular a measuring device from the following group: autorefractor, refractometer, keratometer, aberrometer, wavefront measuring device, optical coherence tomography (OCT) scanner, Scheimpflug camera, ultrasound imaging system, microscope.

Naturally, the ophthalmological laser therapy appliance can also contain a plurality of measuring devices, which are used in succession or simultaneously for the purposes of characterizing the patient's eye.

A further example configuration of the ophthalmological laser therapy appliance moreover comprises an apparatus for automated removal of a tissue from the structure for pressure-reducing bridging of the cornea or from the structure for receiving a shunt implant and/or for automated introduction of a shunt implant into the structure envisaged therefor for the purposes of receiving the latter.

This apparatus for automated removal of a tissue and/or automated introduction of a shunt implant is likewise controlled by the control unit of the ophthalmological laser therapy appliance. The apparatus manipulates the tissue (i.e., as a rule, a tissue part severed from the remainder of the cornea or the sclera or the limbus, which tissue part must be removed from the structure for receiving the shunt implant so that the shunt implant has space therein) and/or the shunt implant by the action of force. Such an action of force can be implemented by application of negative pressure. The application of negative pressure renders the apparatus usable both for removing the tissue and for introducing the shunt implant, for example by using different attachments in order to be able to safely manipulate both the tissue and the shunt implant. However, alternatively, a manipulation by electroadhesion is also possible, in particular when removing tissue.

Such a removal of tissue and/or introduction of a shunt implant by this apparatus is for example monitored using the measuring device of the ophthalmological laser therapy appliance and hence a correct manipulation of the tissue or of the shunt implant by application of the apparatus is ensured. Ideally, there is a gap-free navigation of the apparatus for automated removal of a tissue and/or automated introduction of a shunt implant using the measuring device.

In a planning method for generating control data for an ophthalmological laser therapy appliance, the latter comprising a laser device with a laser source for generating a pulsed laser beam, a focusing apparatus for focusing the pulsed laser beam on a focus, and a scanning apparatus for scanning the focus of the pulsed laser beam in a tissue of a patient's eye, in particular in a cornea, a limbus, and/or a sclera, for modifying, microstructuring or severing the tissue along a scanning pattern of focus spots of the focus of the pulsed laser beam in accordance with the control data, and a control unit for controlling the ophthalmological laser therapy appliance, data of the characterization of the patient's eye, in particular of the cornea, limbus, and/or sclera of the patient's eye, and data of a model of a shunt implant for pressure-reducing bridging of the cornea and/or data of a structure, to be generated in the cornea, the limbus, and/or the sclera, for pressure-reducing bridging of the cornea are provided.

However, further characterization data, in particular structural, can be supplied, such as, for example, specific targets of the surgeon which are relevant to the planning method, for example the tissue regions that should be excluded, in surgeon or patient specific fashion, from processing with a pulsed laser beam, or else characterization data of a measured shunt implant.

The provision of the data for characterizing the patient's eye can be implemented by use of characterizing measurements on the patient's eye by a measuring device, or such patient-specific data can be accessed.

The data for the model of the shunt implant can be provided from a database containing very different shunt implant models, the database moreover containing instructions as to how each of these shunt implant models should be handled in addition to geometric and material data for the shunt implant. This likewise applies to the data of a structure, to be generated in the cornea, the limbus, and/or the sclera, for pressure-reducing bridging of the cornea: For such a structure, too, the database can contain basic models or suggestions, which then only still need to be adapted to the individual patient's eye within the scope of the planning method.

However, alternatively, the data of the model of the shunt implant can also be generated by measuring the shunt implant.

Finally, in a very simple embodiment, significant data of the model of the shunt implant and/or significant data of a structure, to be generated in the cornea, the limbus, and/or the sclera, for pressure-reducing bridging of the cornea can also be entered manually by way of an input mask.

Then, in the planning method according to the invention, control data for the scanning pattern of the focus in a tissue of the patient's eye, in particular in the cornea, the limbus, and/or the sclera, are ascertained from the provided data, the control data rendering the ophthalmological laser therapy appliance controllable in such a way that the structure for pressure-reducing bridging of the cornea and/or the structure for receiving the shunt implant for the pressure-reducing bridging of the cornea can be generated in the tissue of the patient's eye.

The structure for pressure-reducing bridging of the cornea in the tissue of the patient's eye and/or the structure for receiving the shunt implant for pressure-reducing bridging of the cornea is planned in this case within the scope of this planning method and with the aid of the provided data in such a way that subsequently, following the realization of the corresponding structure for pressure-reducing bridging of the cornea and/or the structure for receiving the shunt implant for pressure-reducing bridging of the cornea in the tissue of the patient's eye by application of an ophthalmological laser therapy appliance supplied with these control data, the reception (with the best possible fit) of the shunt implant in the cornea, the limbus, and/or the sclera, i.e., a sliding of this shunt implant into the structure for the reception thereof, is facilitated or a structure for pressure-reducing bridging of the cornea achieves a correspondingly desired drainage effect and the aqueous humor is able to drain in regulated fashion and a pressure between the interior of the eye and the surroundings of the eye can consequently be compensated to the intended extent.

Finally, the control data generated in the planning method are transferred to a control unit of the ophthalmological laser therapy appliance.

The control data, which are transferred to the control unit of the ophthalmological laser therapy appliance, allow the relative position of the focus of the pulsed laser beam to be controlled in space (x, y, z) as a function of time in order to generate the corresponding structures for receiving the shunt implant and/or for pressure-reducing bridging of the cornea in the patient's eye. However, the control data also comprise corresponding laser data such as, for example, the power of the laser at the respective time. Thus, the control data describe a corresponding scanning pattern of focus spots of the focus of the pulsed laser beam in the tissue of the patient's eye. A control data record of control data, generated by the planning method, consequently contains a two-dimensional or three-dimensional pattern as a scanning pattern of focus spots for driving the laser device.

These focus spots—and hence the target points, as already explained above—are arranged in the scanning pattern in such a way here that, when the pulsed laser beam subsequently irradiates the tissue of the patient's eye in accordance with the control data, the structures, described by the scanning pattern, for receiving the shunt implant and/or for pressure-reducing bridging of the cornea in the patient's eye are formed, as a rule, as an incision surface, as a modified or microstructured surface and/or as a modified or microstructured tissue volume or incision volume.

Each focus spot has a focus effective region, in which, when irradiated by the pulsed laser beam, tissue is modified, microstructured or severed apart, with the focus effective regions of adjacent focus spots being able to partly or completely overlap. Here, the tissue in the focus effective region around a focus spot is modified by the pulsed laser. Depending on the type of pulsed laser, a plasma that contributes to the modification of the tissue in the focus effective region may arise in the center of the focus spot.

Here, there can be regions in an incision surface in which the focus effective regions of adjacent focus spots do not overlap completely but only partially such that tissue bridges remain in the incision surface, which tissue bridges can be overcome by a slight subsequent application of force (e.g., by slight pressure on a shunt implant during the insertion thereof). Hence, the structure for receiving the shunt implant in the cornea, the limbus, and/or the sclera is only opened when the shunt implant is being introduced such that an (additional) sterile barrier remains in place until that point. In addition to the relative position of adjacent focus spots with respect to one another, the energy influx, for example, determines whether the focus effective regions of adjacent focus spots overlap completely or incompletely such that there is a complete or incomplete separation of the tissue in the incision surface or a tissue is modified or microstructured accordingly in a volume region.

In an example planning method, the spacing of the focus spots of the focus of the pulsed laser beam and their relative position to one another are taken into account in the scanning pattern.

In addition to the energy input, the spacing and the relative position of the focus spots with respect to one another determines whether there is a complete or incomplete separation of the tissue in this incision surface and/or the scanning pattern describes at least one tissue region microstructured by the pulsed laser beam, which tissue region is filled by focus spots at the focus of the pulsed laser beam, which moves along the scanning pattern, in such a way that the tissue is modified in a focus effective region around the focus spot of the pulsed laser. In relation to the untreated tissue, such a modification or such microstructuring changes the permeability of the corresponding microstructured tissue region to liquids and gases, and consequently also to the aqueous humor to be drained.

Here, following the irradiation by the pulsed laser radiation, the incision surface or the microstructured tissue region can have a different perforation in different regions of the incision surface and/or of the microstructured tissue region: Thus, there can be regions of complete separation next to regions of incomplete separation or regions of pure tissue modification without separation.

In a further an example planning method, the structure for receiving the shunt implant for pressure-reducing bridging of the cornea is embodied such that, following the reception of the shunt implant, a change in the position thereof in the cornea, the limbus, and/or the sclera is prevented, and in particular such that back-sliding following the reception thereof is prevented.

A planning method in which the structure for receiving a shunt implant for pressure-reducing bridging of the cornea is embodied as a "negative" (or optionally as a reduced-sized "negative") of the shunt implant, in particular in which the structure is embodied as a bridge-like structure in the cornea, the limbus, and/or the sclera, in which the shunt implant can be received for example completely, i.e., without protrusion, in a specific configuration as an implant bridge structure, is particularly advantageous according to an example embodiment. This facilitates an insertion with an accurate fit and creates a good and secure hold of the implant in the reception structure.

In a particular configuration of the planning method, for a subsequent step, further control data are generated for driving the laser device to scan the focus of the pulsed laser beam in a shunt implant, received in the patient's eye, for pressure-reducing bridging of the cornea for the purposes of modifying the shunt implant along the scanning pattern of focus spots of the focus of the pulsed laser beam in accordance with the control data, in particular, further control data are generated for a scanning pattern by application of which protrusions of the introduced shunt implant are removed and/or smoothing of the shunt implant is brought about. Here, scanning the focus of the pulsed laser beam in a shunt implant also comprises scanning on a surface of the shunt implant.

In another configuration of the planning method, control data for a structure are generated, said structure having a drainage structure as structure for pressure-reducing bridging of the cornea, which is stabilized by way of light-induced cross-linking.

In one variant of the planning method, at least one access incision is moreover defined from the supplied data, said access incision reaching from the surface of the cornea, the limbus, and/or the sclera to the structure for pressure-reducing bridging of the cornea and/or to the structure for receiving the shunt implant for pressure-reducing bridging of the cornea, and additional control data are generated for driving the laser device for this access incision, by application of which the ophthalmological laser therapy appliance is controllable in such a way that this access incision can be generated in the cornea, the limbus, and/or the sclera of the patient's eye.

In a further configuration of the planning method, the structure for pressure-reducing bridging of the cornea has a cavity and control data for the scanning pattern are generated in such a way that, when scanning the focus of the pulsed laser beam in accordance with the control data, a tissue volume in the cornea, the limbus, and/or the sclera is separated. This tissue volume can for example subsequently be removed through the opening of an access incision.

In an example configuration of the planning method, the data of the characterization of the patient's eye are generated from a measurement of the patient's eye and supplied to the planning device, wherein the data of the characterization of the patient's eye are for example ascertained by use of one or more of the following measurements: an autorefractive measurement, a refractometric measurement, a keratometric measurement, an aberrometer measurement, a wavefront measurement, optical coherence tomography (OCT), a Scheimpflug process, ultrasound imaging, a microscopic measurement.

Additionally, in one variant of the planning method and within the scope of generating the control data, a deformation of the cornea of the patient's eye during laser therapy is taken into account by way of an apparatus for immobilizing the patient's eye, in particular a deformation as a result of affixing the patient's eye to the ophthalmological laser therapy appliance by application of a patient interface, and so the structure for pressure-reducing bridging of the cornea and/or the structure for receiving the shunt implant for pressure-reducing bridging of the cornea is subsequently present in the non-deformed cornea, limbus, and/or sclera.

A shunt implant according to the invention for pressure-reducing bridging of the cornea is characterized by a cross section with a concave cross-sectional area through the shunt implant or through a pressure equalizing element of the shunt implant in a sectional plane extending perpendicular to a surface of the cornea. An example to this end is an implant bridge structure, which is used for better fixability in the tissue of the patient's eye and which, as a rule, offers a plurality of options for developing the pressure-reducing effect.

Incidentally, reference should be made here to the fact that, as a rule, a shunt implant (which develops an outflow or drainage effect) includes the properties of a stent implant (keeping the passage open). A person skilled in the art would usually denote relatively small implants focusing on keeping the passage open as stent implants and would denote slightly larger implants and, in particular, complex implants with a drainage effect as shunt implants.

A shunt implant according to the invention for pressure-reducing bridging of the cornea is furthermore characterized in that it comprises a channel element as a pressure-equalizing element and a fixation element, wherein the fixation element is introduced into the tissue independently of the channel element and the channel element is affixable to the tissue using the fixation element.

In one configuration of the shunt implant according to the invention, the channel element comprises a receiving structure for the fixation element. Here, the channel element is able to be plugged onto the fixation element or the fixation element is able to be introduced into the receiving structure of the channel element.

In a further example configuration of the shunt implant according to the invention, the fixation element contains a tool adapter structure, by use of which the fixation element can easily be positioned with a tool, which engages in the tool adapter structure.

A computer program product according to the invention comprises a program code which, upon its execution on a computer, carries out the above-described planning method for generating control data for an ophthalmological laser therapy appliance, and/or which is readable on an above-described planning device for generating control data, in particular by a processor of such a planning device, and for example on such a planning device for consecutively controlling an ophthalmological laser therapy appliance using the generated control data, and which, when carried out by the planning device, generates control data to operate the ophthalmological laser therapy appliance for treating a tissue of a patient's eye for pressure-reducing bridging of the cornea.

The above-described computer program product is stored on a computer-readable medium according to the invention.

In a method according to the invention for pressure-reducing bridging of the cornea, the above-described planning method is used to generate control data for a scanning pattern of the focus in a tissue of the patient's eye, in particular in the cornea, the limbus, and/or the sclera, for an ophthalmological laser therapy appliance and transfer said to the latter, and the ophthalmological laser therapy appliance is operated with the aid of these control data in order to generate, in the patient's eye, a structure for pressure-reducing bridging of the cornea in the tissue of the patient's eye and/or a structure for receiving the shunt implant for pressure-reducing bridging of the cornea.

Such a method for pressure-reducing bridging of the cornea, in which, following the generation of a structure for receiving a shunt implant in the tissue of the patient's eye, the shunt implant is temporarily or permanently affixed, by application of a bioadhesive, i.e., by application of a biocompatible adhesive, in a structure for receiving the shunt implant, is advantageous according to an example embodiment.

Such a method for pressure-reducing bridging of the cornea, in which, following a generation of a structure for receiving a shunt implant in the tissue of the patient's eye, the shunt implant is not only temporarily or permanently affixed to a structure for receiving a shunt implant but, in the process, the shunt implant is also sealed in the structure for receiving the shunt implant, is particularly advantageous according to an example embodiment. Hence, secondary outflows—i.e., an emergence of liquid from the eye via the structure for receiving the shunt implant—can be prevented.

To this end, the bioadhesive is applied to a peripheral surface of the structure for receiving a shunt implant and/or to a peripheral surface of the shunt implant, with this not having to be implemented over the entire depth of the structure. By contrast, merely a pointwise application of the bioadhesive is sufficient for a temporary or permanent fixation.

Likewise, a bioadhesive, i.e., a biological adhesive, is claimed for use as temporary or permanent fixation of a shunt implant in a structure for receiving the shunt implant in a tissue of a patient's eye. Here, the shunt implant for example is an implant of the type described further above.

Moreover, such a bioadhesive for use as a fixation can for example serve as a seal, as a result of which secondary outflows—i.e., an emergence of liquid from the eye via the structure for receiving the shunt implant—can be prevented and a return migration of germs between the shunt implant and the tissue of the patient's eye can be suppressed even more effectively.

While a bioadhesive for use as a temporary or permanent fixation of the shunt implant in the tissue of the patient's eye in a structure for receiving a shunt implant can also be applied only locally (i.e., not over the entire structure but only in pointwise fashion), if it should be used as a seal, said bioadhesive needs to be applied to at least one peripheral surface of the structure for receiving a shunt implant and/or to one peripheral surface of the shunt implant. However, this need not be implemented over an entire depth of the structure.

Hence, a process is available for a stable introduction of a pressure-reducing stent or shunt implant into the cornea, the limbus, and/or the sclera, which can therefore be brought very precisely—usually in interlocking fashion—into position. Here, the implant can have an individual design in terms of its spatial geometry and can have all spatial degrees of freedom (e.g., indentations, deployable structures) in its surface.

Such a shunt implant forms a so-called miniaturized implant on the scale of the cornea; i.e., it has an axial extent of approximately 500 μm and a lateral extent of less than approximately 1000 μm. In a example configuration, it has a lateral extent of approximately 500 μm, in a further example of approximately 250 μm and ideally of less than 100 μm, sometimes even less than 50 μm.

It ensures that high demands in respect of tightness, positional stability and functional stability are met and ensures the compatibility with the natural functions of the eye (vision, eyelid closure).

Incisions for the shunt implant can also be implemented when incisions are implemented for a cataract surgery or refractive corrections.

It is understood that the features specified above and the features yet to be explained below can be used not only in the specified combinations, but also in other combinations or on their own, without departing from the scope of the present invention.

The intention is to explain the present invention in more detail on the basis of exemplary embodiments on the basis of the attached drawings. In detail:

Figure 1:
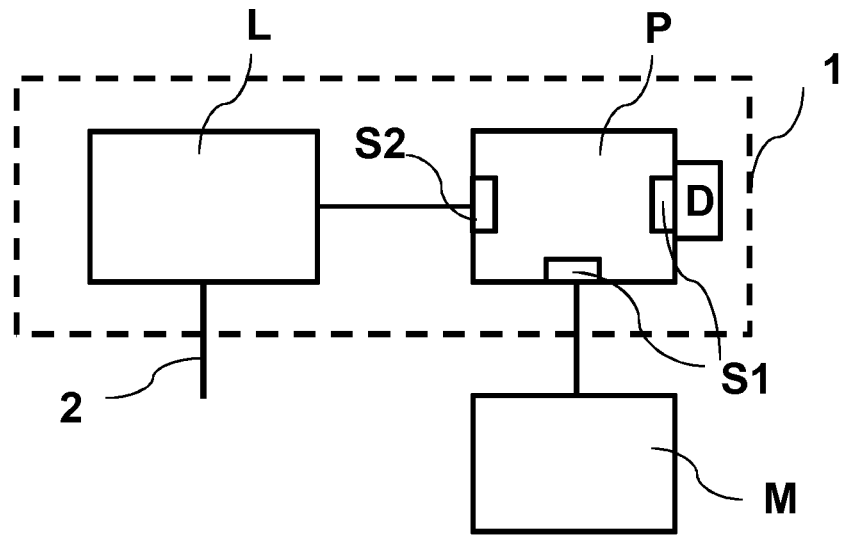
FIG. 1 shows a diagram of a first embodiment of an ophthalmological laser therapy appliance 1 according to the invention.

FIG. 1 schematically shows a first embodiment of the ophthalmological laser therapy appliance 1. In this variant, it comprises at least two devices or modules. A laser device L emits the pulsed laser beam 2 onto the patient's eye 3. Here, the laser device L operates fully automatically; i.e., the laser device L, following an appropriate start signal, starts the deflection of the laser beam 2 and, in the process, produces incision surfaces 24, modified or microstructured areas or modified or microstructured tissue regions 32 in the cornea 16 and/or the sclera 21, which are structured as will still be described below. The control data required for the operation are received by the laser device L in advance as a control data record from a planning device P via communication paths not denoted in any more detail, such as control lines, for example. Naturally, the communication can also be implemented in wireless fashion. As an alternative to direct communication, it is also possible to arrange the planning device P in spatially separated fashion from the laser unit L and to provide a corresponding data transmission channel. The transmission is for example implemented prior to the operation of the laser device L.

For example, the control data record is transmitted to the laser device L of the ophthalmological laser therapy appliance 1 via an interface S2 of the planning device P and, in a further example, an operation of the laser device L is blocked until a valid control data record is present at the laser device L. A valid control data record can be a control data record that, in principle, is suitable for use with the laser device L of the ophthalmological laser therapy appliance 1. However, additionally, the validity can also be linked to further tests being passed, for example whether specifications about the ophthalmological laser therapy appliance 1, e.g., an appliance serial number, or about the patient, e.g., a patient identification number, which are additionally stored in the control data record, correspond to other specifications that, for example, are read at the ophthalmological laser therapy appliance 1 or entered separately as soon as the patient is in the correct position for the operation of the laser device L.

The planning device P generates the control data or the control data record, provided to the laser device L for carrying out the operation, from the supplied measurements data, i.e., the data of the characterization, which are ascertained for the patient's eye 3 to be treated, and from data of a model of a shunt implant 30, 31, 34 for pressure-reducing bridging of the cornea 16 and/or from data of a structure 32, 33, 35, to be generated in the cornea 16, the limbus 14, and/or the sclera 21, for pressure-reducing bridging of the cornea. This is supplied to the planning unit P via interfaces S1.

In the illustrated exemplary embodiment, the measurement data originate from an independent measuring device M, which had previously measured the patient's eye 3. Naturally, the measuring device M can transmit the corresponding measurement data to the planning device P in any suitable way. A direct radio or wired link for example of the measuring device M to the ophthalmological laser therapy appliance 1 in respect of the data transmission, which can be used in one variant, is advantageous in that the use of incorrect measurement data can be excluded with the greatest possible reliability.

The data of the model of a shunt implant 30, 31, 34 for pressure-reducing bridging of the cornea 16 and/or of a structure 32, 33, 35, to be generated in the cornea 16, the limbus 14, and/or the sclera 21, for pressure-reducing bridging of the cornea are supplied from a database D in this case, said database being arranged next to the planning device P and being part of the ophthalmological laser therapy appliance 1.

The control data generated by the planning device P determine the scanning pattern 25 of the focus 7 of the laser device L in the tissue of the patient's eye 3, in particular in the cornea 16, in the limbus, and/or in the sclera 21, said control data rendering the ophthalmological laser therapy appliance 1 controllable in such a way that the structure 32, 33 for pressure-reducing bridging of the cornea 16 can be generated in the tissue of the patient's eye 3 and/or the structure 35 for receiving the shunt implant 30, 31, 34 for the pressure-reducing bridging of the cornea 16 can be generated and—if the control data are used on the ophthalmological laser therapy appliance 1—it is also generated.

The transmission of the supplied data can be implemented by use of memory chips (e.g., by USB or memory stick), magnetic storage units (e.g., disks), wirelessly by radio (e.g., WLAN, UMTS, Bluetooth®) or in wired fashion (e.g., USB, FireWire RS232, CAN bus, Ethernet, etc.). Naturally, the same applies in respect of the data transmission between planning device P and laser device L.

Figure 2:
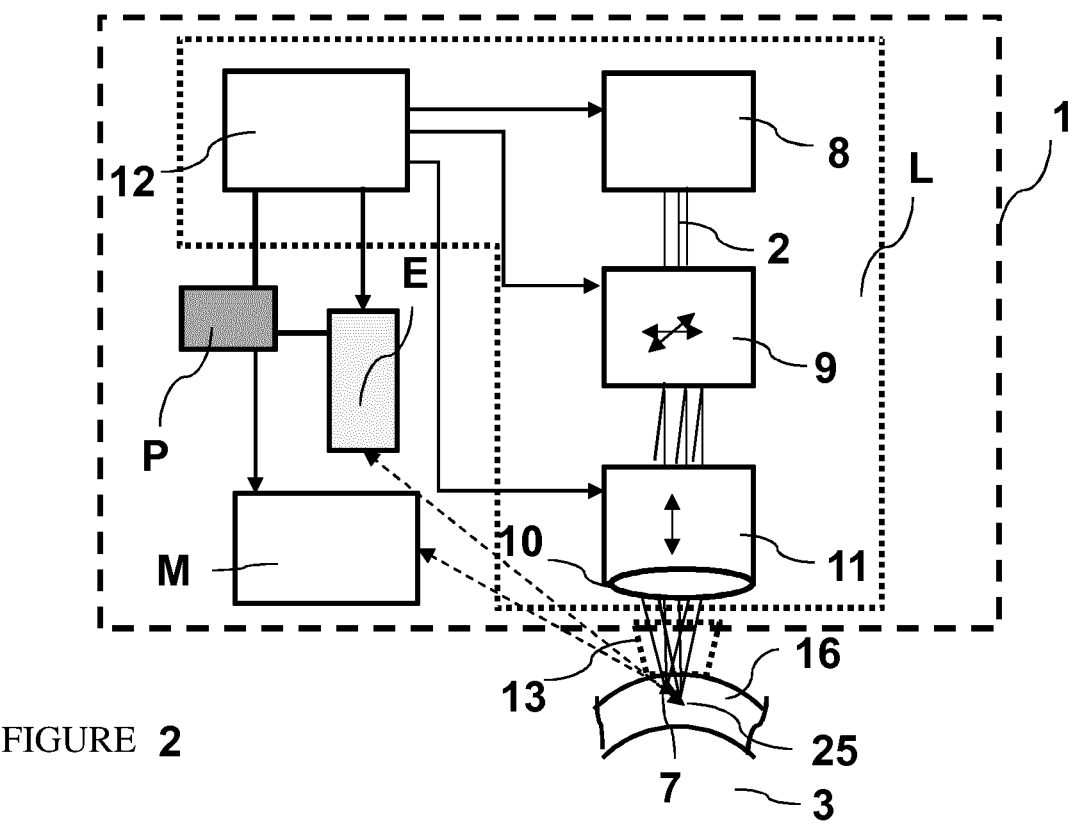
FIG. 2 shows a diagram of a second embodiment of an ophthalmological laser therapy appliance 1 according to the invention.

FIG. 2 shows a diagram of a second embodiment of an ophthalmological laser therapy appliance 1 according to the invention, in which a laser device L and a measuring device M are integrated. This facilitates repeated access to data of the characterization of the patient's eye 3. A planning device P, which satisfies the functions already described above, is integrated into the ophthalmological laser therapy appliance 1 and is in direct communication with the measuring device M and the control unit 12 of the laser device L. Optionally, this embodiment of an ophthalmological laser therapy appliance 1 according to the invention comprises an apparatus E for automated removal of tissue from the structure 32, 33 for pressure-reducing bridging of the cornea or from the structure 35 for receiving a shunt implant 30, 31, 34, 37 and/or for automated introduction of a shunt implant 30, 31, 34, 37, which is likewise controlled by the control unit 12. This apparatus manipulates the tissue to be removed and/or the shunt implant 30, 31, 34, 37 by an application of force by application of negative pressure. To monitor correct manipulation of the tissue or of the shunt implant 30, 31, 34, 37 by the apparatus E, the navigation is implemented using the measuring device M.

In this example of FIG. 2, the elements of the ophthalmological laser therapy appliance 1 and, in particular, of the laser device L comprised by this ophthalmological laser therapy appliance 1 are specified, but, in this case, too, only plotted to the extent that they are required for understanding the focus adjustment. The pulsed laser beam 2 is focused in a focus 7 in the cornea 16 (or in the limbus and/or in the sclera 21) and the relative position of the focus 7 in the cornea 16 (or in the limbus and/or in the sclera 21) is adjusted such that, for the purposes of generating incision surfaces, for the purposes of microstructuring or for the purposes of modifying the tissue and hence for the purposes of generating the structure 32, 33 for pressure-reducing bridging of the cornea 16 in the tissue of the patient's eye 3 and/or the structure 35 for receiving the shunt implant 30, 31, 34 for pressure-reducing bridging of the cornea 16, energy is introduced from pulses of the laser radiation into the tissue of the cornea 16 of the patient's eye 3 at different points or positions, the focus spots 6 of the focus 7 along a scanning pattern 25 of this focus 7. The laser beam 2 is provided as pulsed radiation by a laser 8. Here, the cornea 16 (or the limbus and/or the sclera 21) of the patient's eye 3 is fixed by application of a patient interface 13 to the ophthalmological laser therapy appliance 1.

An xy-scanner 9, which is realized by two substantially orthogonally deflecting galvanometer mirrors in one variant, deflects the pulsed laser beam 2 emanating from the laser source 8 in two dimensions. Consequently, the xy-scanner 9 brings about an adjustment of the relative position of the focus 7 substantially perpendicular to the chief direction of incidence of the pulsed laser beam 2 into the cornea 16. In addition to the xy-scanner 9, a z-scanner 11 is provided for adjusting the depth position, said z-scanner being embodied as an adjustable telescope, for example. The z-scanner 11 ensures that the z-position of the relative position of the focus 7, i.e., the position thereof along the optical axis of incidence, is modified. The z-scanner 11 can be disposed upstream or downstream of the xy-scanner 9. The coordinates denoted below by x, y, z therefore relate to the deflection of the relative position of the focus 7.

The assignment of the individual coordinates to spatial directions is not essential for the functional principle of the ophthalmological laser therapy appliance 1; however, for the purposes of simpler description, z always denotes the coordinate along the optical axis of incidence of the pulsed laser beam 2 below and x and y denote two mutually orthogonal coordinates in a plane perpendicular to the direction of incidence of the laser beam 2. Naturally, a person skilled in the art knows that the relative position of the focus 7 in the cornea 16 can also be described in three dimensions by other coordinate systems; in particular, this need not necessarily be a rectangular coordinate system. Thus, it is not mandatory for the xy-scanner 9 to deflect about axes that are perpendicular to one another; rather, it is possible to use any scanner that is able to adjust the focus 7 in a plane not containing the axis of incidence of the laser beam 2. Consequently, it is also possible to use oblique-angled coordinate systems, or else non-Cartesian coordinate systems.

For the purposes of controlling the relative position of the focus 7, the xy-scanner 9 and the z-scanner 11, which together realize a specific example of a three-dimensional scanning apparatus 9, 11, are actuated by a controller 12 via lines not denoted in any more detail. The same applies to the laser source 8. The controller 12 ensures a suitable synchronous operation of the laser source 8 and the three-dimensional scanning apparatus 9, 11, realized by the xy-scanner 9 and the z-scanner 11 in exemplary fashion, such that the relative position of the focus 7 in the cornea 16 (or in the limbus and/or the sclera 21) is adjusted such that, ultimately, the structure 32, 33 for pressure-reducing bridging of the cornea 16 and/or the structure 35 for receiving the shunt implant 30, 31, 34 for pressure-reducing bridging of the cornea 16 in the tissue of the patient's eye 3 is achieved by scanning predetermined target points, the focus spots 6, on the scanning pattern 25, in each case by radiating the pulsed laser beam 2 onto this target point and hence generating an incision surface 24, a modified or microstructured area or a modified or microstructured tissue volume 32, by application of which the structure 32, 33 for pressure-reducing bridging of the cornea 16 and/or the structure 35 for receiving the shunt implant 30, 31, 34 for pressure-reducing bridging of the cornea 16 is formed.

The controller 12 operates according to predetermined control data, which predetermine the target points for the focus adjustment, i.e., the scanning of the focus 7. As a rule, the control data are combined in a control data record. In one embodiment, the latter predetermines the coordinates of the target points as a pattern, wherein the sequence of the target points in the control data record sets the stringing together of the focus positions and hence, consequently, a trajectory—the scanning pattern 25. In one embodiment, the control data record contains the target points as specific manipulated variables for the scanning mechanism, e.g., for the xy-scanner 9 and the z-scanner 11. In one embodiment, it also contains all data required for operating the laser source 8 in addition to the geometric data of the respective target points. For the purposes of preparing the ophthalmic surgical method, i.e., before the actual operation method can be carried out, the target points and preferably for example also the sequence thereof in the scanning pattern 25 are determined. Thus, there must be preplanning of the surgical intervention to the extent that the control data for the ophthalmological laser therapy appliance 1 are ascertained, the application of which then obtains an optimal, in terms of for the patient's eye 3 and the desired shunt implant 30, structure 32, 33 for pressure-reducing bridging of the cornea 16 and/or structure 35 for receiving the shunt implant 30, 31, 34. This is achieved by the planning device according to the invention and the planning method according to the invention.

Figure 3:
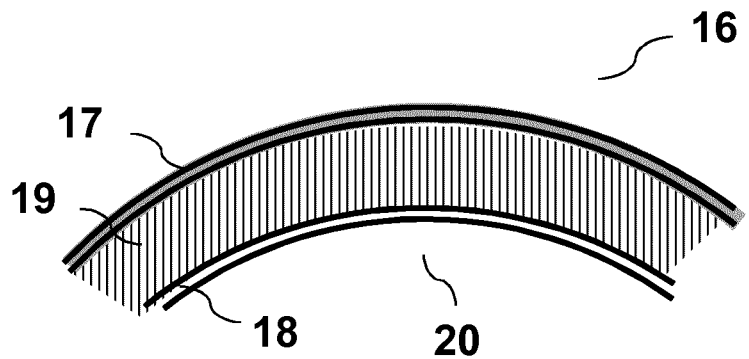
FIG. 3 shows the basic structure of the cornea.

FIG. 3 shows the basic structure of the cornea 16. The "central" layer, extending over the substantial portion of its depth, is the stroma 19. To the outside, the latter is terminated by the epithelium 17; by contrast, in the inward direction toward the anterior chamber 20 of the eye, the endothelium 18 forms the termination.

Figure 4A:
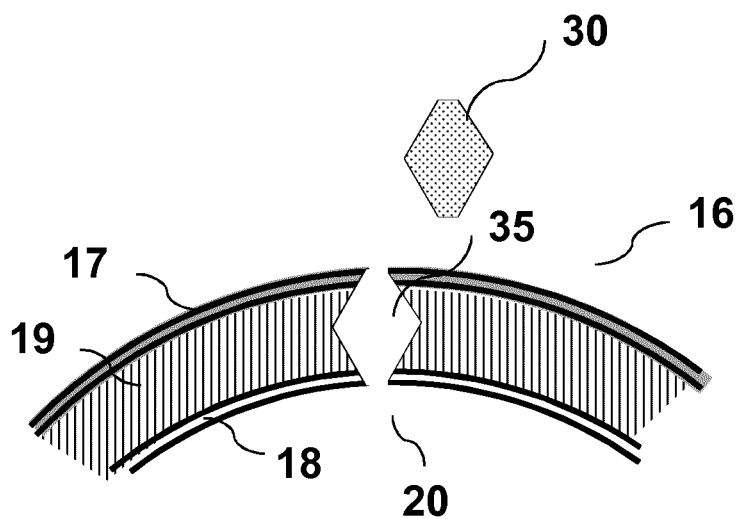
FIGS. 4a and 4b show a first embodiment of a structure, generated using a planning device according to the invention and/or a planning method according to the invention, for receiving the shunt implant for pressure-reducing bridging of the cornea, and a first embodiment of a shunt implant.
Figure 4B:
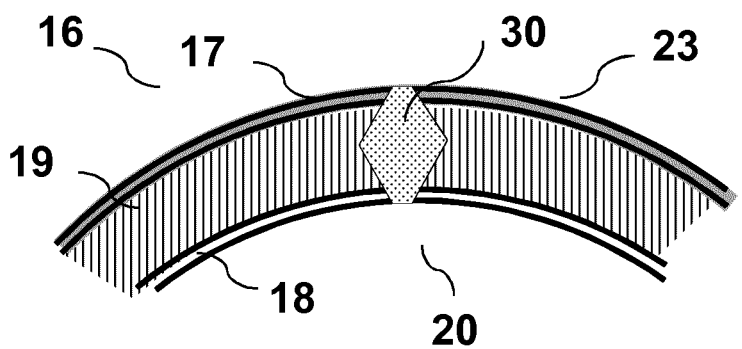

FIGS. 4a and 4b show a first embodiment of a structure 35, generated using a planning device P according to the invention and/or a planning method according to the invention, for receiving the shunt implant 30 for pressure-reducing bridging of the cornea 16 and a first embodiment of a shunt implant 30. Using a laser device L of an ophthalmological laser therapy appliance 1, which has received appropriate control data from the planning device P, a cornea 16 is processed such that a three-dimensional structure 35 for receiving the shunt implant 30 arises throughout the entire cornea, said structure forming the negative to this minimally invasive shunt implant 30 with accurate fit (and with a slight reduction in size in order to achieve pretension), as shown in FIG. 4a.

FIG. 4b then shows the cornea 16 with the shunt implant 30, the latter for example having elastic properties. It has now been inserted and fills the structure 35, generated by the laser processing, for receiving it. For example, the implant 30 is pretensioned in an injector tool in this case and inserted into the structure 35 for receiving the shunt implant 30.

Figure 5A:
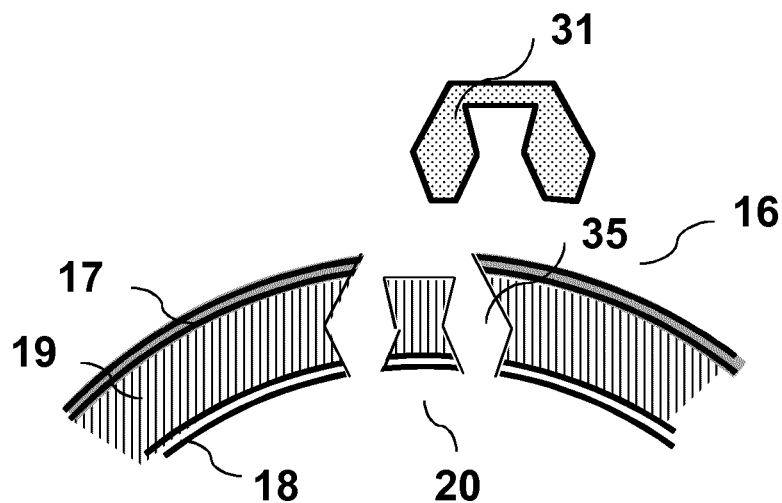
FIGS. 5a and 5b show a second embodiment of a structure, generated using a planning device according to the invention and/or a planning method according to the invention, for receiving the shunt implant for pressure-reducing bridging of the cornea, and a second embodiment of a shunt implant.
Figure 5B:
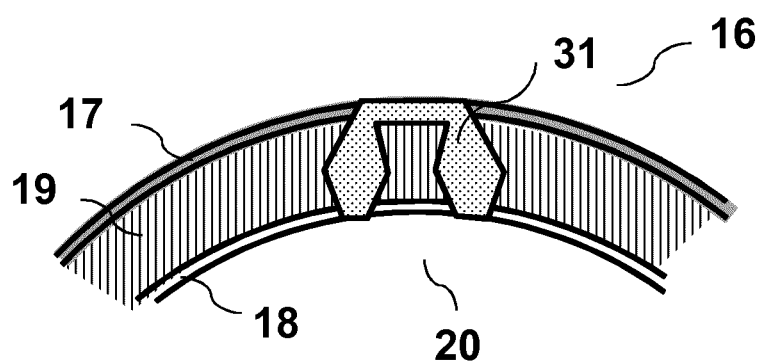

FIGS. 5a and 5b show a second embodiment of a structure 35, generated using a planning device P according to the invention and/or a planning method according to the invention, for receiving the shunt implant 30, 31 for pressure-reducing bridging of the cornea 16, and a second embodiment of a shunt implant 30, 31. Using a laser device L of an ophthalmological laser therapy appliance 1, which has received appropriate control data from the planning device P, a cornea 16 is processed such that a three-dimensional, bridge-like structure 35 for receiving the implant bridge structure 31 of shunt implant 30 arises throughout the entire cornea, the implant bridge structure 31 being able to be received with an accurate fit in said three-dimensional, bridge-like structure. This provides the implant 30 with a more stable hold in the cornea 16, it is positioned there in a manner maintaining its function and, following the implantation, a plurality of drainage channels arise for draining the aqueous humor and consequently for pressure-reducing bridging of the cornea 16.

Figure 6:
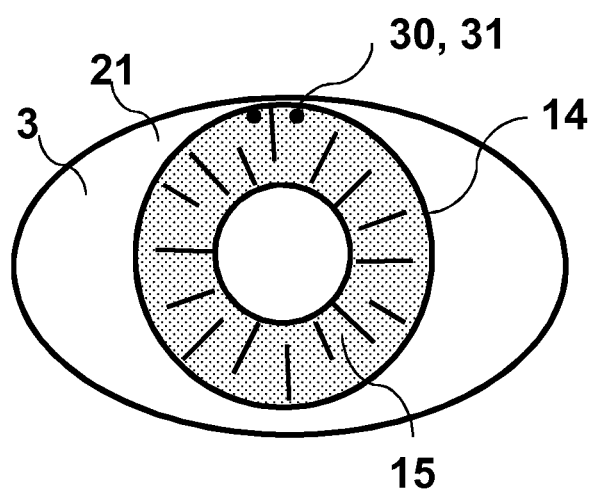
FIG. 6 shows a possible relative position of the shunt implant in a patient's eye.

FIG. 6 shows a possible relative position of the shunt implant 30, 31 in a patient's eye 3: Such an implant 30, 31 is for example introduced in the edge region of the cornea 16, in the limbus 14 and/or in the sclera 21, i.e., outside of the optical zone of the cornea, so as not impair the vision. Additionally, a plurality of these implants 30 can be realized at a plurality of points in the patient's eye 3. In order to adapt the aqueous humor drainage, these implants can also be introduced over long time intervals, depending on the course of the disease; i.e., a patient's eye 3 is able to be treated multiple times by this method and corresponding interventions can be planned multiple times in succession using the planning device P, with data from preceding operations optionally also being able to be taken into account in subsequent operations.

Figure 7A:
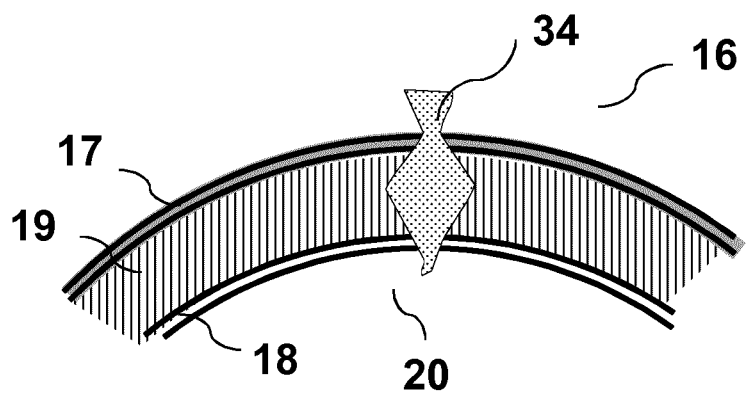
FIGS. 7a and 7b show a third embodiment of a structure, generated using a planning device according to the invention and/or a planning method according to the invention, for receiving the shunt implant for pressure-reducing bridging of the cornea, and a third embodiment of a shunt implant.
Figure 7B:
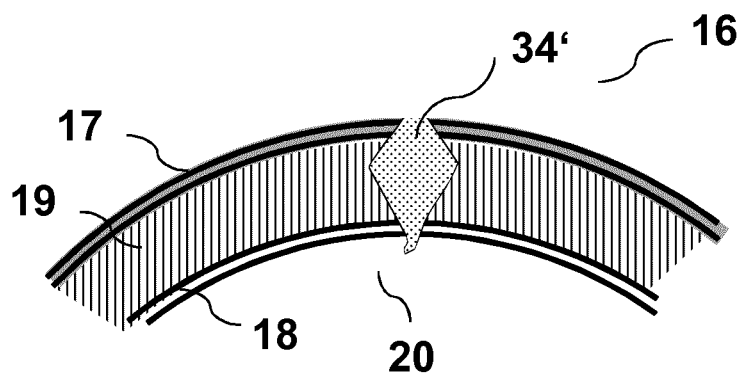

FIGS. 7a and 7b show a third embodiment of a structure 35, generated using a planning device P according to the invention and/or a planning method according to the invention, for receiving the shunt implant 30, 34, 34' for pressure-reducing bridging of the cornea 16, and a third embodiment of a shunt implant 30, 34, 34'.

FIG. 7a shows a shunt implant 30, 34 which has been introduced into the cornea of a patient's eye and which protrudes beyond the outer surface 22 of the cornea, in particular beyond the epithelium, in its final position. This is perceived as uncomfortable and would lead to irritation to the eye lid over time. Therefore, after the shunt implant 30, 34 has been introduced into the cornea, laser processing (e.g., ablation) is used to remove the protrusions (FIG. 7b) and/or carry out smoothing such that the shunt implant 30, 34' is flush with the surface of the cornea 16 and physiological effects can no longer be felt.

Therefore, the shunt implant 30, 34 can be treated by the laser device L of the ophthalmological laser therapy appliance 1 in this embodiment, just like the tissue of the patient's eye 3. In particular, portions on the inserted shunt implant 30, 34 are ablated using the laser. In this case, the planning device P likewise generates control data for processing the shunt implant 30, 34.

Such an option can also be used for subsequent post-processing of the inserted shunt implant 30, 34 in order to prevent this from being overgrown by the continuously regrowing epithelial cell layers.

In particular, this option or a basic post-processing option is usable to repeatedly process an inserted shunt implant 30, 34 and/or a structure 32, 33, generated in the tissue of the patient's eye 3, for pressure-reducing bridging of the cornea 16 in order to adapt these individually to the patient and/or on the basis of the course of the disease, for example by adapting by way of a laser processing the flow rate of the implant 30, 34 or of the structure 32, 33 for pressure-reducing bridging of the cornea 16.

Figure 8:
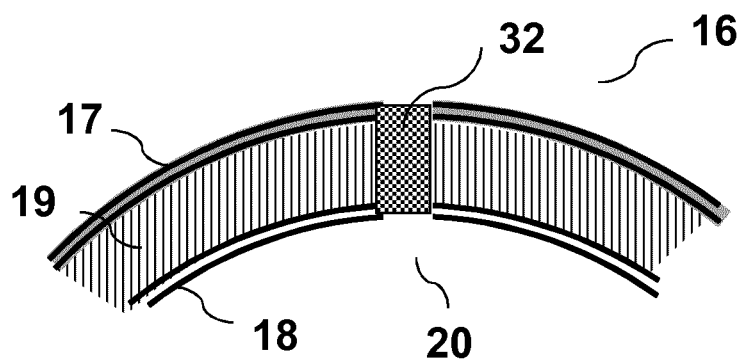
FIG. 8 shows a fourth embodiment of a structure, generated using a planning device according to the invention and/or a planning method according to the invention, for pressure-reducing bridging of the cornea.

FIG. 8 shows a fourth embodiment of a structure 32, generated using a planning device P according to the invention and/or a planning method according to the invention, for pressure-reducing bridging of the cornea 16. In this embodiment, a tissue-inherent drainage structure alone is generated by modification and/or microstructuring of a tissue volume 32; potentially, this can be stabilized by way of light-induced cross-linking. Such cross-linking of the tissue structures of the modified or microstructured tissue volume 32 can also be used by irradiation, for example by adding riboflavin, to reduce undesirable scarring or wound healing reactions. This generates a drainage structure or, more generally, a stable structure 32 for pressure-reducing bridging of the cornea 16 in the cornea 16, the limbus 14, and/or the sclera 21, which is stable over a relatively long period of time of one or more years, and said structure can be adapted individually to the patient or to the clinical picture and is embodied in such a way that an ingress of bacteria or germs is suppressed. The introduction of a shunt implant 30 is not envisaged in this embodiment.

Figure 9A:
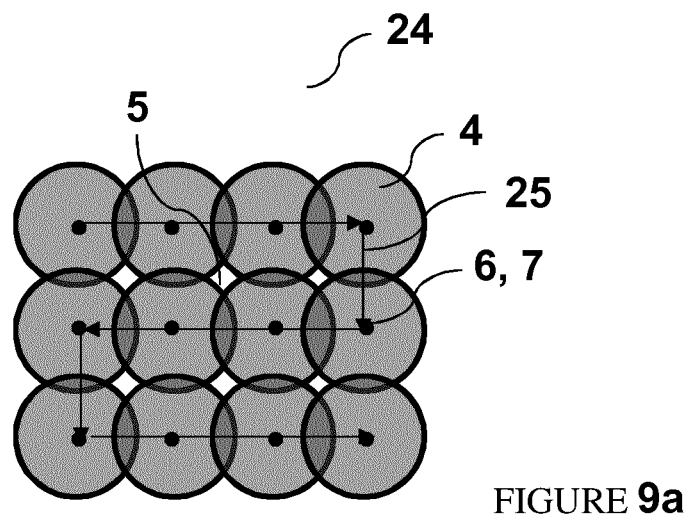
FIGS. 9a to 9c show different embodiments of scanning patterns of focus spots of the focus of a pulsed laser beam.
Figure 9B:
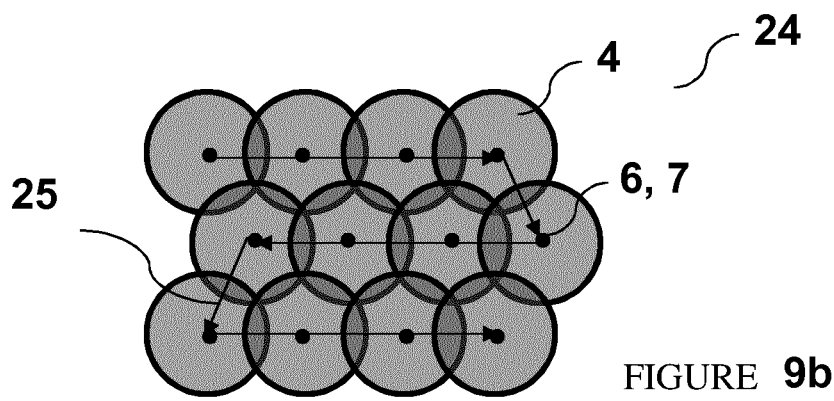
Figure 9C:
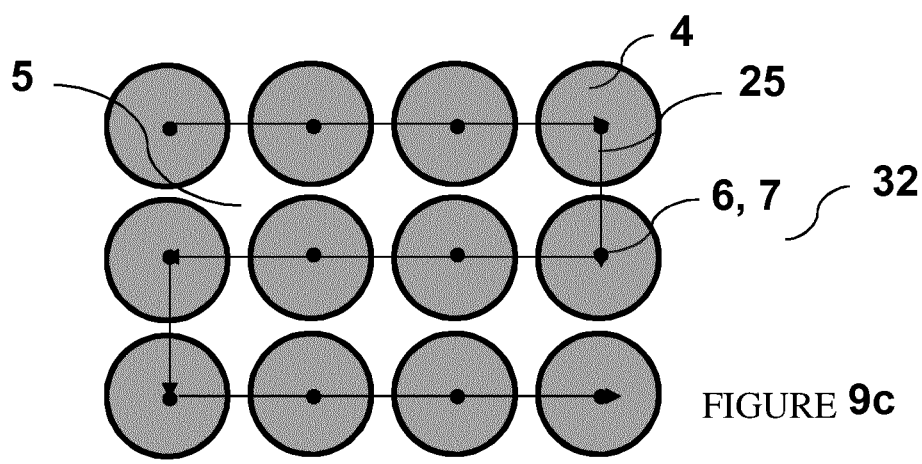

FIGS. 9a to 9c show different embodiments of scanning patterns 25 of focus spots 6 of the focus 7 of a pulsed laser beam 2. Here, FIG. 9a shows an incompletely separated incision surface 24, in which tissue bridges 5 remain, and FIG. 9b shows a completely separated incision surface 24, in which no tissue bridges 5 remain, while FIG. 9c represents an area of a modified tissue volume 32, in which the focus spots 6 with the respective focus effective regions 4 thereof bring about a local change in the tissue, the tissue bridges 5 in this case being not only locally linked with one another but forming a far-reaching and stable network, which cannot be destroyed with little pressure.

Figure 10:
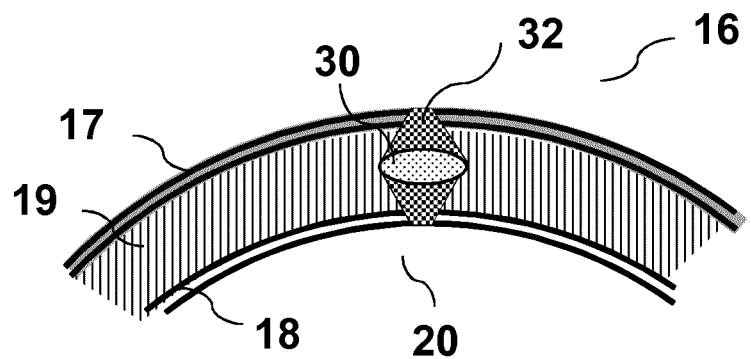
FIG. 10 shows a fifth embodiment of a structure, generated using a planning device according to the invention and/or a planning method according to the invention, for pressure-reducing bridging of the cornea and a structure for receiving the shunt implant for pressure-reducing bridging of the cornea, and a fourth embodiment of a shunt implant.

FIG. 10 shows a fifth embodiment of a structure 32, generated using a planning device P according to the invention and/or a planning method according to the invention, for pressure-reducing bridging of the cornea and a structure 35 for receiving the shunt implant 30 for pressure-reducing bridging of the cornea 16 with an inserted shunt implant 30, and a fourth embodiment of a shunt implant 30. Here, the introduction of a shunt implant 30 is combined with a modification or microstructuring of a tissue volume 32. The interaction of the shunt implant 30 with the structure 32 for pressure-reducing bridging of the cornea 16 brings about the desired drainage effect. In this embodiment, the tasks of the shunt implant 30 are, in particular, the exercise of a filter effect, the securing of the pressure gradient and the suppression of the ingress of germs into the anterior chamber 20.

Figure 11A:
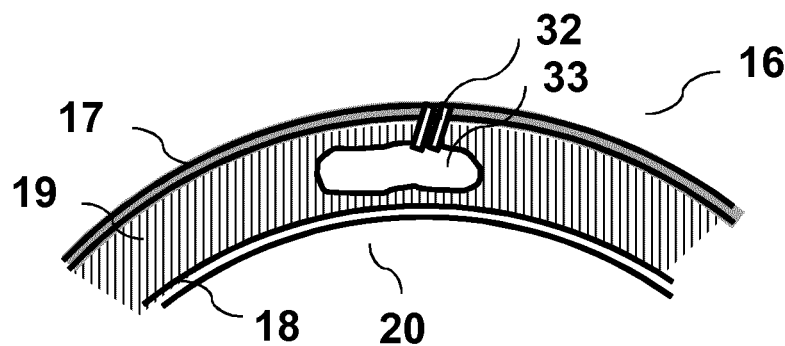
FIGS. 11a and 11b show a sixth embodiment of a structure, generated using a planning device according to the invention and/or a planning method according to the invention, for pressure-reducing bridging of the cornea and a structure for receiving the shunt implant for pressure-reducing bridging of the cornea, and a fifth embodiment of a shunt implant.
Figure 11B:
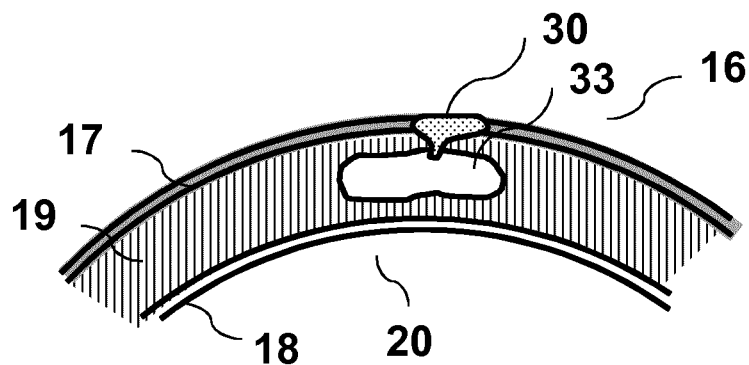
Figure 12A:
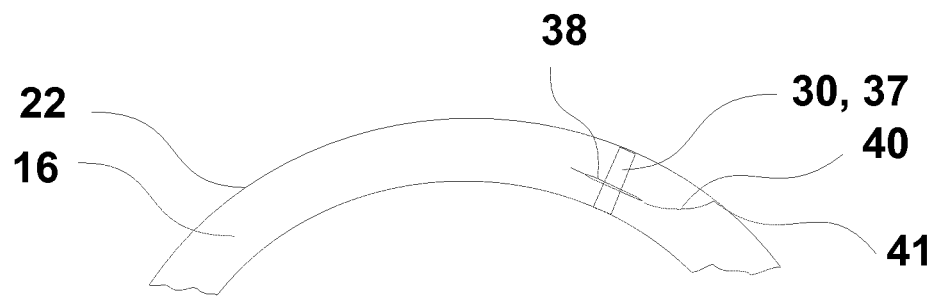
FIGS. 12a to 12d show a seventh embodiment of a structure, generated using a planning device according to the invention and/or a planning method according to the invention, for receiving the shunt implant for pressure-reducing bridging of the cornea, and a sixth embodiment of a shunt implant.
Figure 12B:
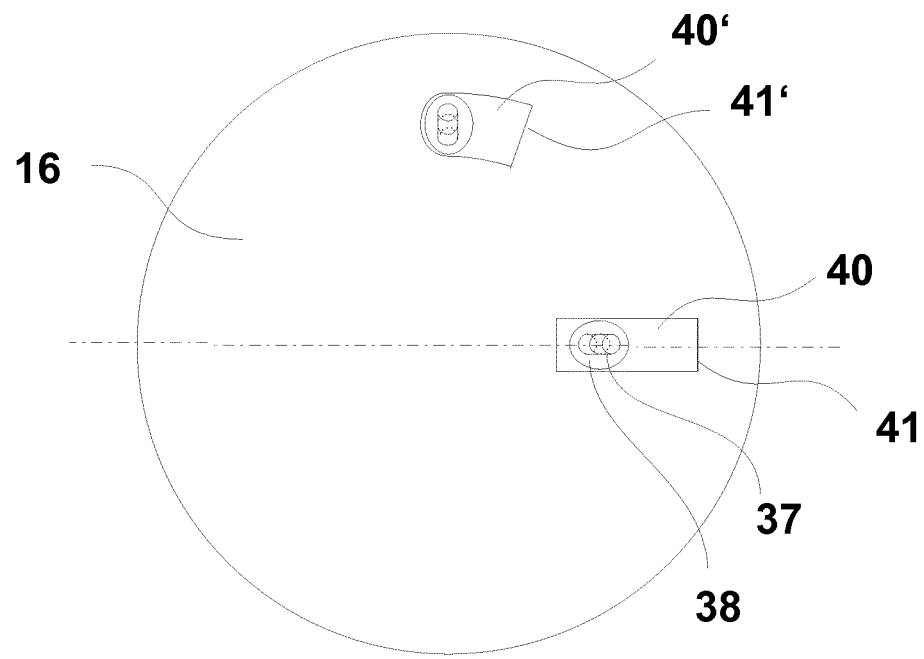
Figure 12C:
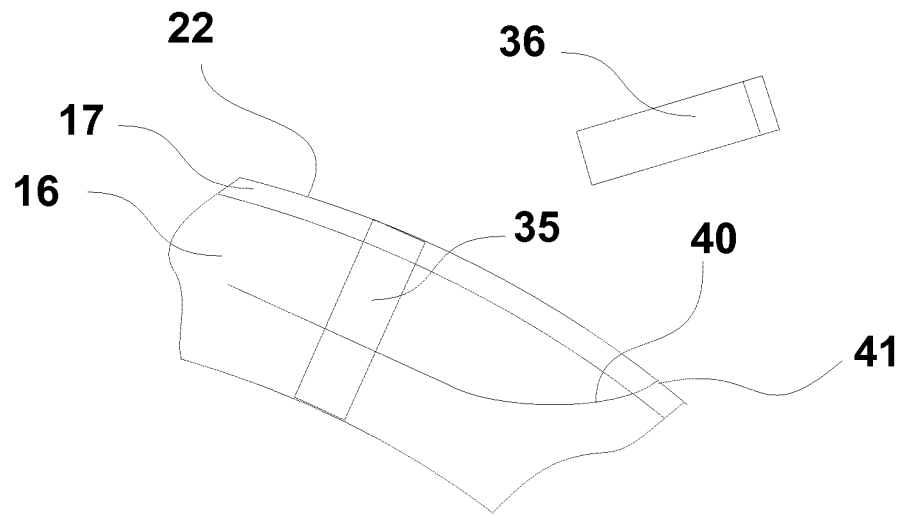
Figure 12D:
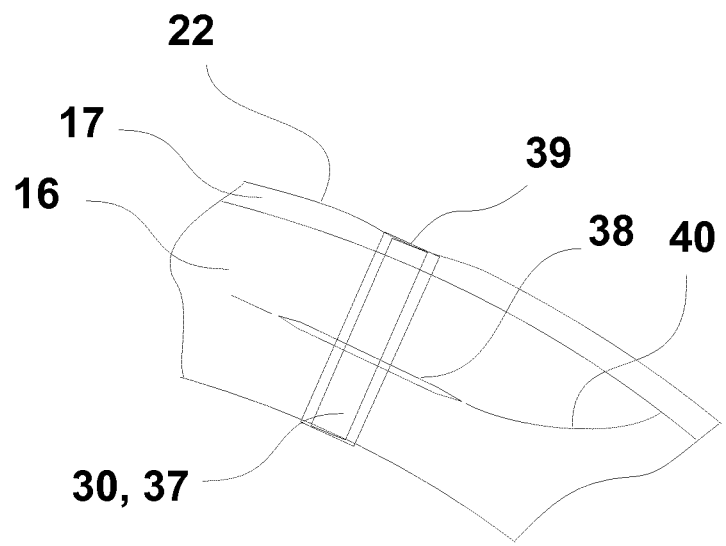

FIGS. 11a and 11b illustrate a sixth embodiment of a structure 32, 33, generated using a planning device P according to the invention and/or a planning method according to the invention, for pressure-reducing bridging of the cornea and a structure 35 for receiving the shunt implant 35 for pressure-reducing bridging of the cornea 16, and a fifth embodiment of a shunt implant 30. In this embodiment, a cavity 33 is generated in the cornea 16, the limbus 14, and/or the sclera 21, said cavity serving as a collection reservoir for the aqueous humor in order to assist the drainage of the latter. The drainage in the direction of the surface of the cornea 16 or sclera 21, and hence also toward the tear fluid on the epithelium 17, can be further assisted by further laser processing of the cornea 16, of the limbus 14, and/or of the sclera 21 for the purposes of creating an active drain 32 (FIG. 11a) or by the introduction of a further shunt implant 30 (FIG. 11b).

FIGS. 12a to 12d show a seventh embodiment of a structure 35, generated using a planning device P according to the invention and/or a planning method according to the invention, for receiving the shunt implant 30 for pressure-reducing bridging of the cornea 16, and a sixth embodiment of a shunt implant 30, 37. The shunt implant 30, 37 used here is a multi-part implant which, by application of an additional fixation element 38, allows "reversible" locking of the shunt implant 30, 37. The fixation element 38 is introduced via an access incision 40. The shunt implant 30 embodied as a channel element 37, which has a channel 39 and which is responsible for the drainage or pressure-reducing effect, is introduced via the structure 35 for receiving the shunt implant 30, 37. Channel element 37 and fixation element 38 are mechanically coupled. This method is reversible: The shunt implant to 30, 37 is reachable through the access incision 40 at all times. Only the epithelial layer 17 on the front side 22 of the cornea 16 grows together again and must be surgically opened again. Through the access incision 40, the surgeon can reach, release and remove the fixation element 38 with a tool. Subsequently, the channel element 37 can also be removed. A new channel element 37, i.e., a new shunt implant 30, can be introduced into the already existing structure 35 for receiving the shunt implant 30 and it can be affixed using a new fixation element 38, which in turn has been inserted via the access incision 40.

Figure 13A:
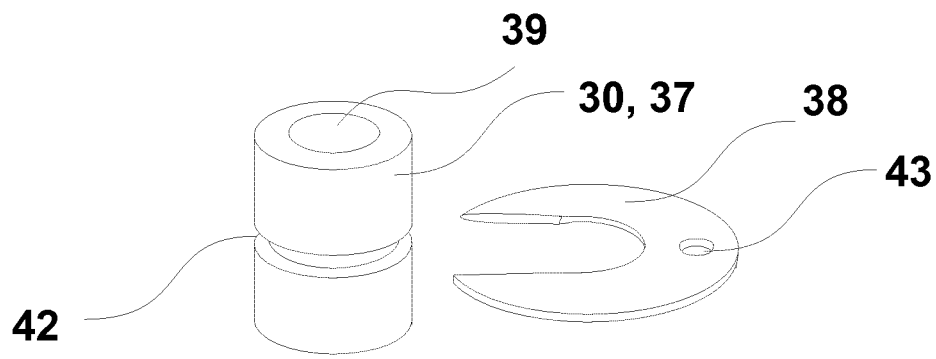
FIGS. 13a and 13b show a seventh and eighth embodiment of a shunt implant.
Figure 13B:
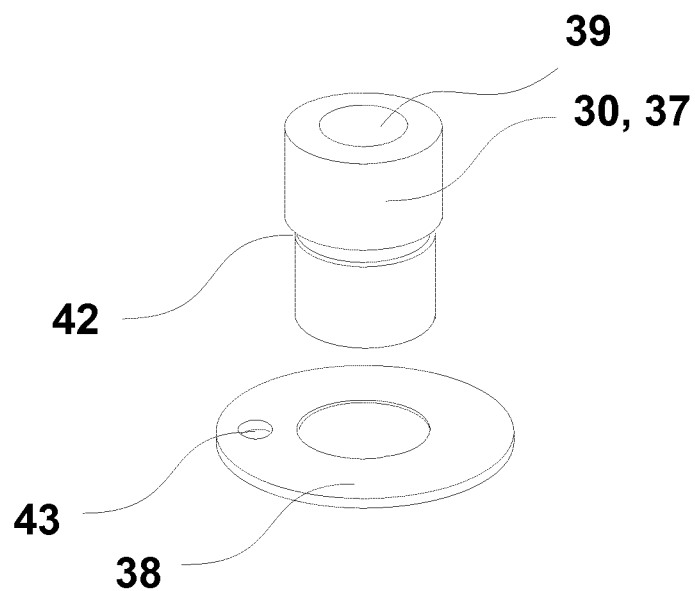

FIGS. 13a and 13b explain a seventh and an eighth embodiment of a shunt implant 30 in the form of a multi-part implant, which comprises a channel element 37 and a fixation element 38. The channel elements 37 of both embodiments of the multi-part shunt implant each have a receiving structure 42. In the case of FIG. 13a, the channel element 37 is initially introduced into the structure 35 for receiving the shunt implant 30, 37 and the fixation element 38 is subsequently brought to the channel element 37 via the access incision 40 and introduced into the receiving structure 42 in order to affix it in this position. By contrast, in the case of FIG. 13b, a fixation element 38 is initially inserted through the access incision 40 and positioned in such a way that, when inserting the channel element 37 into the structure 35 for receiving the shunt implant 30, said channel element is plugged onto the fixation element 38 and, in the process, the channel element 37 with the receiving structure 42 comes to a stop in the fixation element 38. In order to allow the fixation element 38 to be appropriately "grasped" for insertion and positioning and, in the case of an exchange, for removal via the access incision 40, the fixation element 38 contains a tool adapter structure 43, i.e., a structure or an element on which the surgeon can grasp the fixation element 38 with a tool. Said structure is only illustrated in simplified fashion here and, in the specific embodiment, may facilitate interlocking or force-fit connections between tool and fixation element 38 of the shunt implant 30, 37.

In this case, the aforementioned features of the invention, which are explained in various exemplary embodiments, can be used not only in the combinations specified in an exemplary manner but also in other combinations or on their own, without departing from the scope of the present invention.

A description of an apparatus relating to method features is analogously applicable to the corresponding method with respect to these features, while method features correspondingly represent functional features of the apparatus described.

The invention claimed is:

1. A planning device for generating control data for an ophthalmological laser therapy appliance, the laser therapy appliance comprising a laser device with a laser source that generates a pulsed laser beam, with a focusing apparatus that focuses the pulsed laser beam on a focus, and with a scanning apparatus that scans the focus of the pulsed laser beam in a tissue of a patient's eye, including a cornea, a limbus, and/or a sclera, that modifies microstructures or severs the tissue along a scanning pattern of focus spots of the focus of the pulsed laser beam in accordance with the control data, and a control unit that controls the ophthalmological laser therapy appliance by application of the control data, wherein the planning device comprises a first interface that supplies data of a characterization of the patient's eye, including the cornea, the limbus, and/or the sclera of the patient's eye, and that supplies data of a model of a shunt implant for pressure-reducing bridging of the cornea and/or data of a structure, to be generated in the cornea, the limbus, and/or the sclera, for pressure-reducing bridging of the cornea, and a second interface that transfers the control data to a control unit of the ophthalmological laser therapy appliance, wherein the planning device is embodied to generate control data for the scanning pattern of the focus in a tissue of the patient's eye, including the cornea, the limbus and/or the sclera, from the supplied data, the control data rendering the ophthalmological laser therapy appliance controllable such that the structure for pressure-reducing bridging of the cornea and/or the structure for receiving the shunt implant for pressure-reducing bridging of the cornea is generated in the tissue of the patient's eye.

2. The planning device as claimed in claim 1, wherein the scanning pattern describes at least one incision surface, which is filled by focus spots of the focus of the pulsed laser beam, which moves along the scanning pattern, such that there is complete or incomplete separation of the tissue at this incision surface, and/or the scanning pattern describes at least one tissue region that has been microstructured by the pulsed laser beam, said tissue region being filled by focus spots of the focus of the pulsed laser beam, which moves along the scanning pattern, in such a way that the tissue of this tissue region is modified in a focus effective region around the focus spot of the pulsed laser.

3. The planning device as claimed in claim 1, wherein the structure for receiving the shunt implant for pressure-reducing bridging of the cornea is embodied to receive the shunt implant in such a way that a subsequent change in the position thereof in the cornea, the limbus, and/or the sclera is inhibited.

4. The planning device as claimed in claim 3, wherein the structure for receiving the shunt implant for pressure-reducing bridging of the cornea is embodied to receive the shunt implant in such a way that a subsequent change in the position thereof in the cornea, the limbus, and/or the sclera is inhibited in such a way that back-sliding following the reception thereof is inhibited.

5. The planning device as claimed in claim 1, wherein the structure for receiving the shunt implant for pressure-reducing bridging of the cornea is embodied as a "negative" of the shunt implant.

6. The planning device as claimed in claim 5, wherein the structure for receiving the shunt implant for pressure-reducing bridging of the cornea is embodied as a "negative" of the shunt implant that, in terms of the dimensions of the structure for receiving the shunt implant, has been slightly reduced in comparison with the dimensions of the shunt implant.

7. The planning device as claimed in claim 1, wherein the structure for receiving the shunt implant for pressure-reducing bridging of the cornea is embodied as a bridge-like structure in the cornea, the limbus, and/or the sclera, in which the shunt implant can be received completely or partially in a specific configuration as an implant bridge structure.

8. The planning device as claimed in claim 1, furthermore embodied to generate, for a subsequent step, further control data for driving the laser device to scan the focus of the pulsed laser beam in a shunt implant for pressure-reducing bridging of the cornea, received in the patient's eye, for the purposes of modifying the shunt implant along a scanning pattern of focus spots of the focus of the pulsed laser beam in accordance with the control data.

9. The planning device as claimed in claim 8, configured to generate the further control data for the subsequent step in such a way that protrusions of the received shunt implant are removed and/or the shunt implant is smoothed.

10. The planning device as claimed in claim 1, wherein the structure for pressure-reducing bridging of the cornea has a drainage structure, which is stabilized by application of light-induced cross-linking.

11. The planning device as claimed in claim 1, configured to moreover define at least one access incision from the supplied data, said access incision reaching from the surface of the cornea, the limbus, and/or the sclera to the structure for pressure-reducing bridging of the cornea and/or to the structure for receiving the shunt implant for pressure-reducing bridging of the cornea, and generate additional control data for driving the laser device for this access incision, by application of which the ophthalmological laser therapy appliance is controllable in such a way that this access incision is generated in the cornea, the limbus, and/or the sclera of the patient's eye.

12. The planning device as claimed in claim 1, wherein the structure for pressure-reducing bridging of the cornea has a cavity and the control data for the scanning pattern are generated such that the scan pattern renders a tissue volume in the cornea, the limbus, and/or the sclera separable, said tissue volume subsequently optionally being removable through the opening of an access incision.

13. The planning device as claimed in claim 1, further comprising a measuring device connected to the first interface, said measuring device producing the data of the characterization of the patient's eye from a measurement of the patient's eye and supplying said data of the characterization to the planning device.

14. The planning device as claimed in claim 13, wherein the measuring device comprises one or more of the following apparatuses: an autorefractor, a refractometer, a keratometer, an aberrometer, a wavefront measuring device, an optical coherence tomography (OCT) scanner, a Scheimpflug camera, an ultrasound imaging system, and a microscope.

15. The planning device as claimed in claim 1, further embodied to generate the control data to take account of a deformation of the cornea, of the limbus, and/or of the sclera of the patient's eye during laser therapy by way of an apparatus for immobilizing the patient's eye, including a deformation of the cornea, the limbus, and/or the sclera as a result of affixing the patient's eye to the ophthalmological laser therapy appliance by use of a patient interface, including a contact glass or a liquid patient interface, such that the structure for pressure-reducing bridging of the cornea and/or the structure for receiving the shunt implant for pressure-reducing bridging of the cornea is present in the non-deformed cornea, limbus, and/or sclera.

16. An ophthalmological laser therapy appliance for treatment of a tissue of a patient's eye for pressure-reducing bridging of the cornea, comprising:
a laser device with a laser source that generates a pulsed laser beam, a focusing apparatus that focuses the pulsed laser beam at a focus, and a scanning apparatus that scans the focus of the pulsed laser beam in a tissue of a patient's eye, including in a cornea, a limbus, and/or a sclera, to modify, microstructure or sever the tissue along a scanning pattern of focus spots of the focus of the pulsed laser beam, which is determined by control data,
a control unit for controlling the ophthalmological laser therapy appliance by application of the control data, and
a planning device that generates the control data, as claimed in claim 1.

17. The ophthalmological laser therapy appliance as claimed in claim 16, further comprising a measuring device that generates data of the characterization of the patient's eye, the measuring device being selected from a group consisting of: an autorefractor, a refractometer, a keratometer, an aberrometer, a wavefront measuring device, an optical coherence tomography (OCT) scanner, a Scheimpflug camera, an ultrasound imaging system and a microscope.

18. The ophthalmological laser therapy appliance as claimed in claim 16, further comprising an apparatus that accomplishes automated removal of tissue from the structure for pressure-reducing bridging of the cornea or from the structure for receiving the shunt implant and/or for automated introduction of the shunt implant into the structure that receives the shunt implant.

19. A planning method for generating control data for an ophthalmological laser therapy appliance, the ophthalmological laser therapy appliance comprising a laser device with a laser source that generates a pulsed laser beam, a focusing apparatus that focuses the pulsed laser beam at a focus, and a scanning apparatus that scans the focus of the pulsed laser beam in a tissue of a patient's eye, including in a cornea, a limbus, and/or a sclera, that modifies, microstructures or severs the tissue along a scanning pattern of focus spots of the focus of the pulsed laser beam in accordance with the control data, and a control unit that for controls the ophthalmological laser therapy appliance by application of the control data, the planning method comprising:

providing data of a characterization of the patient's eye, including of the cornea, limbus, and/or sclera of the patient's eye, and data of a model of a shunt implant for pressure-reducing bridging of the cornea and/or data of a structure, to be generated in the cornea, the limbus, and/or the sclera, for pressure-reducing bridging of the cornea;

ascertaining control data for the scanning pattern of the focus in a tissue of the patient's eye, including in the cornea, the limbus, and/or the sclera, from the data provided, the control data rendering the ophthalmological laser therapy appliance controllable such that the structure for pressure-reducing bridging of the cornea is generated in the tissue of the patient's eye and/or the structure for receiving the shunt implant for pressure-reducing bridging of the cornea is generated; and transferring the control data to the control unit of the ophthalmological laser therapy appliance.

20. A method for pressure-reducing bridging of the cornea, comprising applying a planning method as claimed in claim 19, generating control data for a scanning pattern of the focus in a tissue of the patient's eye, including in the cornea, the limbus, and/or the sclera, for an ophthalmological laser therapy appliance and transferring the control data to the ophthalmological laser therapy appliance; and operating the ophthalmological laser therapy appliance with the aid of the control data to generate, in a patient's eye, a structure for pressure-reducing bridging of the cornea in the tissue of the patient's eye and/or a structure for receiving a shunt implant for pressure-reducing bridging of the cornea.

21. A computer program product with program code which, upon its execution on a computer, carries out a planning method for generating control data for an ophthalmological laser therapy appliance which is readable on a planning device for generating control data as claimed claim 1, by a processor of a planning device, and on the planning device for consecutively controlling an ophthalmological laser therapy appliance using the generated control data, and which, when carried out by the planning device, generates control data to operate the ophthalmological laser therapy appliance for treating a tissue of a patient's eye for pressure-reducing bridging of the cornea.

* * * * *

UNITED STATES PATENT AND TRADEMARK OFFICE
CERTIFICATE OF CORRECTION

| | |
|---|---|
| PATENT NO. | : 11,833,080 B2 |
| APPLICATION NO. | : 16/978605 |
| DATED | : December 5, 2023 |
| INVENTOR(S) | : Hacker et al. |

Page 1 of 1

It is certified that error appears in the above-identified patent and that said Letters Patent is hereby corrected as shown below:

In the Specification

Column 1, Line 12, delete "application claims" and insert -- claims --

Column 1, Line 62, delete "(TOP)." and insert -- (IOP). --

Column 8, Line 12, delete "slowly" and insert -- and slowly --

Column 23, Line 54, delete "manner" and insert -- manner that --

Column 24, Line 17, delete "eye lid" and insert -- eyelid --

In the Claims

Column 30, Line 26, in Claim 21, delete "claimed claim" and insert -- claimed in claim --

Signed and Sealed this
Twenty-fourth Day of December, 2024

Derrick Brent
*Acting Director of the United States Patent and Trademark Office*